(12) United States Patent
Flora

(10) Patent No.: US 7,726,308 B1
(45) Date of Patent: Jun. 1, 2010

(54) APPARATUS AND METHOD FOR RESPIRATORY DRUG DELIVERY

(76) Inventor: Maurino Flora, 4589 Encanto Way, San Jose, CA (US) 95135

( * ) Notice: Subject to any disclaimer, the term of this patent is extended or adjusted under 35 U.S.C. 154(b) by 1009 days.

(21) Appl. No.: 11/265,689

(22) Filed: Nov. 1, 2005

Related U.S. Application Data

(63) Continuation-in-part of application No. 10/435,425, filed on May 9, 2003, now Pat. No. 6,971,385.

(51) Int. Cl.
*A61M 11/00* (2006.01)
(52) U.S. Cl. .............................. 128/203.21; 128/205.21
(58) Field of Classification Search ............ 128/200.22, 128/203.21, 205.21; 239/302–304, 308–311, 239/271, 272; 222/4, 5, 82, 83, 83.5, 85, 222/86, 129
See application file for complete search history.

(56) References Cited

U.S. PATENT DOCUMENTS

| | | | |
|---|---|---|---|
| 4,934,358 A | 6/1990 | Nilsson et al. | |
| 5,002,048 A | 3/1991 | Makiej, Jr. | |
| 5,007,419 A | 4/1991 | Weinstein et al. | |
| 5,169,029 A | 12/1992 | Behar et al. | |
| 5,273,190 A | 12/1993 | Lund | |
| 5,287,850 A | 2/1994 | Haber et al. | |
| 5,293,865 A | 3/1994 | Altner et al. | |
| 5,437,267 A | 8/1995 | Weinstein et al. | |
| 5,488,946 A | 2/1996 | Calhoun et al. | |
| 5,535,736 A | 7/1996 | Jzaw | |
| 5,544,646 A * | 8/1996 | Lloyd et al. | 128/200.14 |
| 5,823,181 A | 10/1998 | Shih | |
| 5,875,776 A | 3/1999 | Vaghefi | |
| 6,070,573 A | 6/2000 | Howe et al. | |
| 6,149,873 A | 11/2000 | Potter et al. | |
| 6,347,725 B1 | 2/2002 | Yoakim et al. | |
| 6,488,894 B1 | 12/2002 | Miethe et al. | |
| 6,543,448 B1 | 4/2003 | Smith et al. | |
| 6,571,790 B1 | 6/2003 | Weinstein | |
| 6,901,929 B2 | 6/2005 | Burr et al. | |
| 6,923,175 B2 | 8/2005 | Poole et al. | |
| 6,971,385 B1 * | 12/2005 | Flora | 128/203.21 |

\* cited by examiner

*Primary Examiner*—Steven O Douglas
(74) *Attorney, Agent, or Firm*—Fernandez & Associates, LLP

(57) ABSTRACT

Apparatus and method for respiratory drug delivery using cartridge containing drug and propellant. User inserts cartridge into body of apparatus and activates a mechanism for opening drug compartment and propellant compartment, resulting in mixing and de-agglomeration of drug for respiratory delivery.

17 Claims, 27 Drawing Sheets

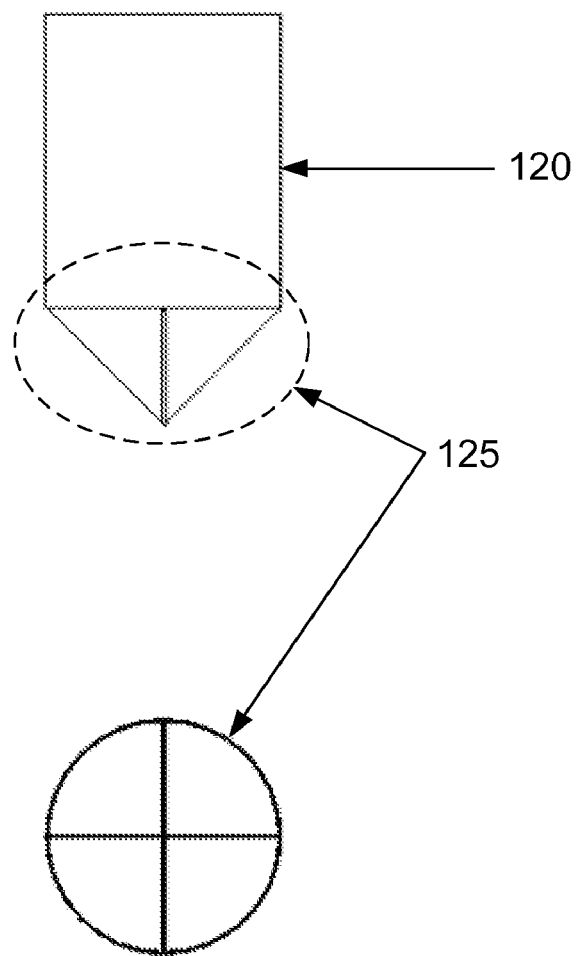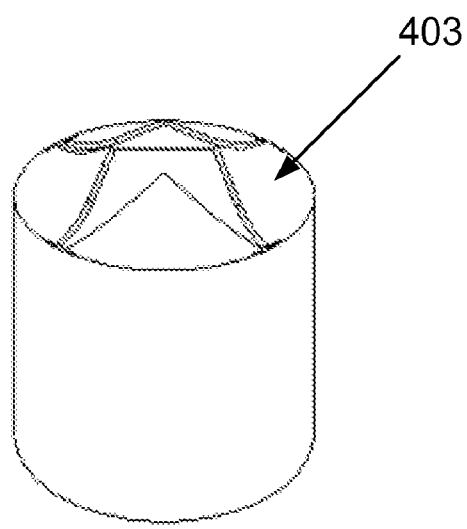
FIG. 3g

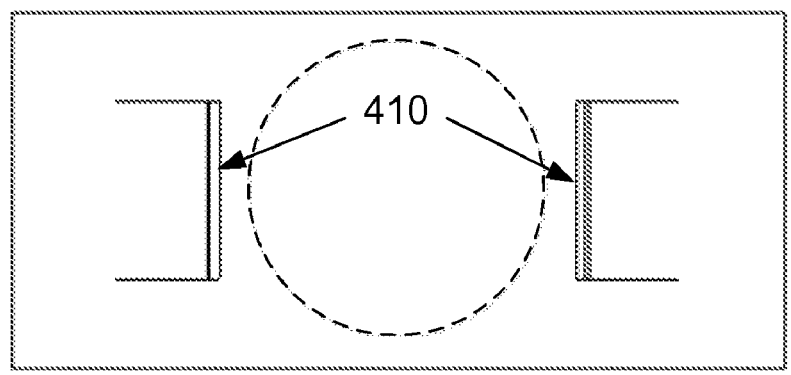
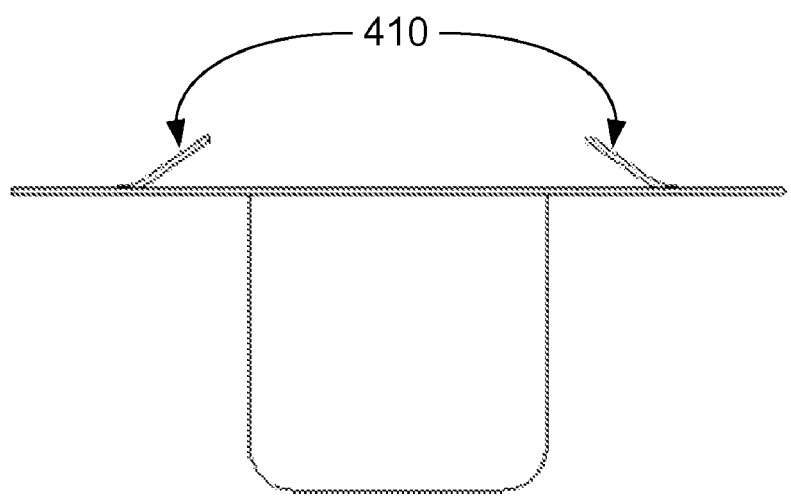
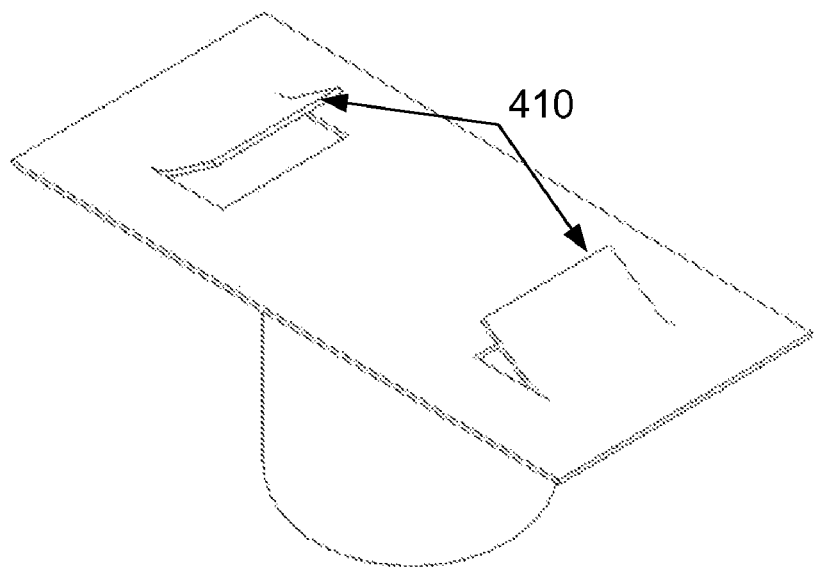
FIG. 4g

```
┌─────────────────────────┐
│    PLACE CARTRIDGE      │ 701
└───────────┬─────────────┘
            ▼
┌─────────────────────────┐
│     PIERCE DRUG         │ 702
│     COMPARTMENT         │
└───────────┬─────────────┘
            ▼
┌─────────────────────────┐
│   PIERCE PROPELLANT     │ 703
│     COMPARTMENT         │
└───────────┬─────────────┘
            ▼
┌─────────────────────────┐
│    AEROSOLIZE DRUG      │ 704
└─────────────────────────┘
```

*FIG. 7*

APPARATUS AND METHOD FOR RESPIRATORY DRUG DELIVERY

RELATED APPLICATIONS

This application is a continuation in part of a prior application Ser. No. 10/435,425, filed May 9, 2003 now U.S. Pat. No. 6,971,385, the disclosure of which is incorporated herein by reference in its entirety, the benefits of the filing dates of which are hereby claimed under 35 U.S.C. §120.

FIELD OF INVENTION

Invention relates to drug delivery systems, and in particular to respiratory drug delivery systems.

BACKGROUND OF INVENTION

For many drugs and treatment needs respiratory drug delivery represents an attractive or unique solution. Delivery of drugs by inhalation, however, is often challenging for a number of reasons. Especially for solid drugs, one challenge is often the design of an appropriate system used for drug delivery. Powdered drugs generally need to be aerosolized before inhalation, a process often requiring systems with high operation reliability and reproducibility for consistent and effective drug delivery.

Several respiratory drug delivery systems have been employed, but they usually have one or more undesirable features. Some delivery systems are bulky, making their transportation inconvenient and thus potentially compromising treatment compliance. Some delivery systems are very expensive to produce, making their adoption unlikely even for routine use for chronic conditions. Some devices contain a pump to pressurize air, which could require a large number of parts and moving parts, with the associated high cost of production, expected wear and tear, as well as challenges for young or old users, or patients suffering from conditions such as clubbed fingers. Inconsistency of the delivered dose is a common shortcoming of present delivery devices, as might be the need of forceful inspiratory flow rate. Time dependent dose variability is most often due to either device reliability (wear and tear) or, for some devices, progressive decrease of drug canister pressure. Furthermore, the percentage of the aerosolized drug that reaches the lung for deposition is often variable, and some systems cannot be easily scaled for child or adult use.

Accordingly, there is a need for improved respiratory drug delivery devices and methods. Ideally, new devices should be compact for portability and to ensure good treatment compliance by patients. Devices should also be inexpensive to the point where they are disposable or routinely replaceable, or contain disposable parts that ensure inexpensive long-term operation. Respiratory drug delivery systems should be easy to use by any group of patients, and should reproducibly generate the required dose of aerosolized drug. Operation of drug delivery devices should not require forceful inspiration. Furthermore, devices are needed that are easily adaptable for the needs of adult or pediatric patients.

SUMMARY OF INVENTION

Generally, the disclosed invention relates to an apparatus and methods for respiratory drug delivery. Typically it is based on using a cartridge having drug and propellant compartments.

In some aspects the invention relates to a cartridge for aerosolizing drugs. The cartridge typically has a drug compartment containing a single dose of a drug. Some embodiments have more than one drug compartment, such as two or more drug sub-compartments, for example for co-administration of drugs. The cartridge also has a propellant compartment containing a propellant in a quantity suitable for aerosolizing the drug in the drug compartment. A common membrane typically joins the drug compartment and the propellant compartment, which may play a role in operation of the systems for which it is intended. In some embodiments the cartridge also comprises a chaser compartment containing a chaser to drive the flow of drug/propellant aerosol. The chaser compartment may be joined to the propellant compartment by a chaser-propellant membrane.

In other aspect the invention relates to systems for respiratory delivery of drugs contained in the disclosed cartridges. The systems or devices typically contain a cartridge holder for holding the cartridge, and a body with tubing for piercing the cartridge. Assembly of the cartridge holder and body in some embodiments can be by a holder thread and a body thread, and assembly positions the pierce tubing for piercing the drug compartment of the cartridge and subsequently the propellant compartment, and, in some embodiments, subsequently a chaser compartment. In some embodiments insertion of the pierce tubing through the drug compartment, the common membrane, and possibly the chaser-propellant membrane is accomplished by continued engagement of the holder thread and the body thread.

In other aspects the invention relates to systems for respiratory delivery of drug in cartridges with different designs. Accordingly, the systems have a propellant chamber with a propellant releasing mechanism for an initial operational step. A propellant tube connects the propellant chamber to the drug compartment, and a drug ejection tube for transporting the drug from the drug compartment to a body for respiratory delivery. When the system is operated propellant is released from the propellant compartment of the cartridge to the propellant chamber of the system, then through the propellant tube into the drug compartment and then through the drug ejection tube into the body.

In yet other aspects the invention relates to cartridges with a puncture resistant, flexible cover. The cartridges also have drug and propellant compartments as mentioned above. A common membrane joins the drug and propellant compartments, and the membrane is pressure sensitive. In addition, the propellant compartment is partly enveloped within the cover. Thus, when a predetermined amount of pressure is applied to the cover, the common membrane breaks, which is useful in related methods and devices. In some embodiments the drug compartment also has a drug ejection membrane that is sensitive to a lower pressure than the common membrane. Thus, breaking of the common membrane results in immediate breaking of the drug ejection membrane, before the pressure in the drug compartment reaches equilibrium with the pressure in the propellant compartment.

In some aspects the invention relates to systems for respiratory delivery of drugs contained in cartridges encased in puncture resistant flexible covers. The systems are made up of a body with a cartridge chamber and a cartridge chamber constricting mechanism. When operated the cartridge chamber constricting mechanism applies additional pressure to the propellant compartment via the cover so as to reach or exceed the predetermined pressure level to which the common membrane is sensitive. In some embodiments the systems comprise a piercing mechanism for piercing the drug ejection membrane prior to applying pressure to the cover.

In other aspects the invention relates to methods for respiratory drug delivery. One such method involves providing a cartridge with a puncture resistant flexible cover, as referred to above, and constricting the cover to break the common membrane. As a result, the aerosolized drug is ejected through the drug ejection membrane and made available for respiratory delivery. As an alternative, piercing of the drug membrane is performed before constriction of the propellant compartment.

In other embodiments the invention relates to respiratory drug delivery system and kits with a propellant tank of a fixed volume, intended to contain a propellant in a quantity suitable for aerosolizing the single dose of a drug. The tank typically has a propellant filling valve and a release valve. The system also has a drug chamber for holding a single drug dose. The drug chamber has a drug ejection opening and is in fluid communication to the release valve of the propellant tank. Opening the release valve of the tank causes the propellant to flow through the drug chamber and to eject aerosolized drug through the drug ejection opening. A syringe for filling the propellant tank can be included.

Cartridges, devices, and methods presented can typically be based on inexpensive manufacturing processes, yet enable respiratory drug delivery results with remarkably high consistency.

BRIEF DESCRIPTION OF DRAWINGS

FIG. 1-*b* is a diagram illustrating a respiratory drug delivery system in closed position, according to one embodiment of the present invention.

FIG. 2-*b* is a diagram illustrating bent mouthpiece, according to one embodiments of the present invention.

FIG. 2-*c* is a diagram illustrating grooved mouthpiece, according to one embodiments of the present invention.

FIG. 2-*d* is a diagram illustrating a respiratory drug delivery system with optional spacer, according to one embodiment of the present invention.

FIG. 3-*b*1 and 3-*b*2 are diagrams illustrating a cross-section of a multi-tubing piercing mechanism, according to one embodiment of the present invention.

FIG. 3-*c* is a diagram illustrating cross-section of bumped piercing mechanism, according to one embodiment of the present invention.

FIG. 3-*d* is a diagram illustrating necked cross-section of pierce tubing, according to one embodiment of the present invention.

FIG. 3-*e* is a diagram illustrating detail of piercing head, according to one embodiment of the present invention.

FIG. 3-*f* is a diagram showing simulation of propellant and drug flow through pierce tubing, according to one embodiment of the present invention.

FIG. 3-*g* is a diagram illustrating a tip of the pierce head and corresponding membrane puncture, according to one embodiment of the present invention.

FIG. 3-*h* is a diagram illustrating a disposable cartridge with spring-loaded plunger mechanism, according to one embodiment of the present invention.

FIG. 3-*i* is a diagram illustrating a disposable cartridge with compressed-elastomer piercing mechanism, according to one embodiment of the present invention.

FIG. 3-*j* is a diagram illustrating a reusable cartridge with spring-loaded plunging mechanism, according to one embodiment of the present invention.

FIG. 3-*k* is a diagram illustrating a reusable cartridge with spring-loaded piercing mechanism, according to one embodiment of the present invention.

FIG. 4-*b* is a diagram illustrating a divided drug or propellant compartment, according to one embodiment of the present invention.

FIG. 4-*c* is a diagram illustrating a drug cartridge with a drug reservoir, according to one embodiment of the present invention.

FIG. 4-*d* is a diagram illustrating a drug cartridge with two drug compartments and one gas compartment.

FIG. 4-*e* is a diagram illustrating a multi-dose rotary cartridge configuration, according to one embodiment of the present invention.

FIG. 4-*f* is a diagram illustrating a roll-up linear cartridge configuration, according to one embodiment of the present invention.

FIG. 4-*g* is a diagram illustrating a cartridge configuration with flow resistance flaps, according to one embodiment of the present invention.

FIG. 5-*b* is a diagram illustrating a micro-version of the respiratory drug delivery system in closed position, according to one embodiment of the present invention.

FIG. 7 is a flow chart illustrating a method for respiratory drug delivery, according to one embodiment of the present invention.

FIG. 9-*b* shows an embodiment of a cartridge chamber with a constricting mechanism.

DETAILED DESCRIPTION OF PREFERRED EMBODIMENTS

Figure 1A:
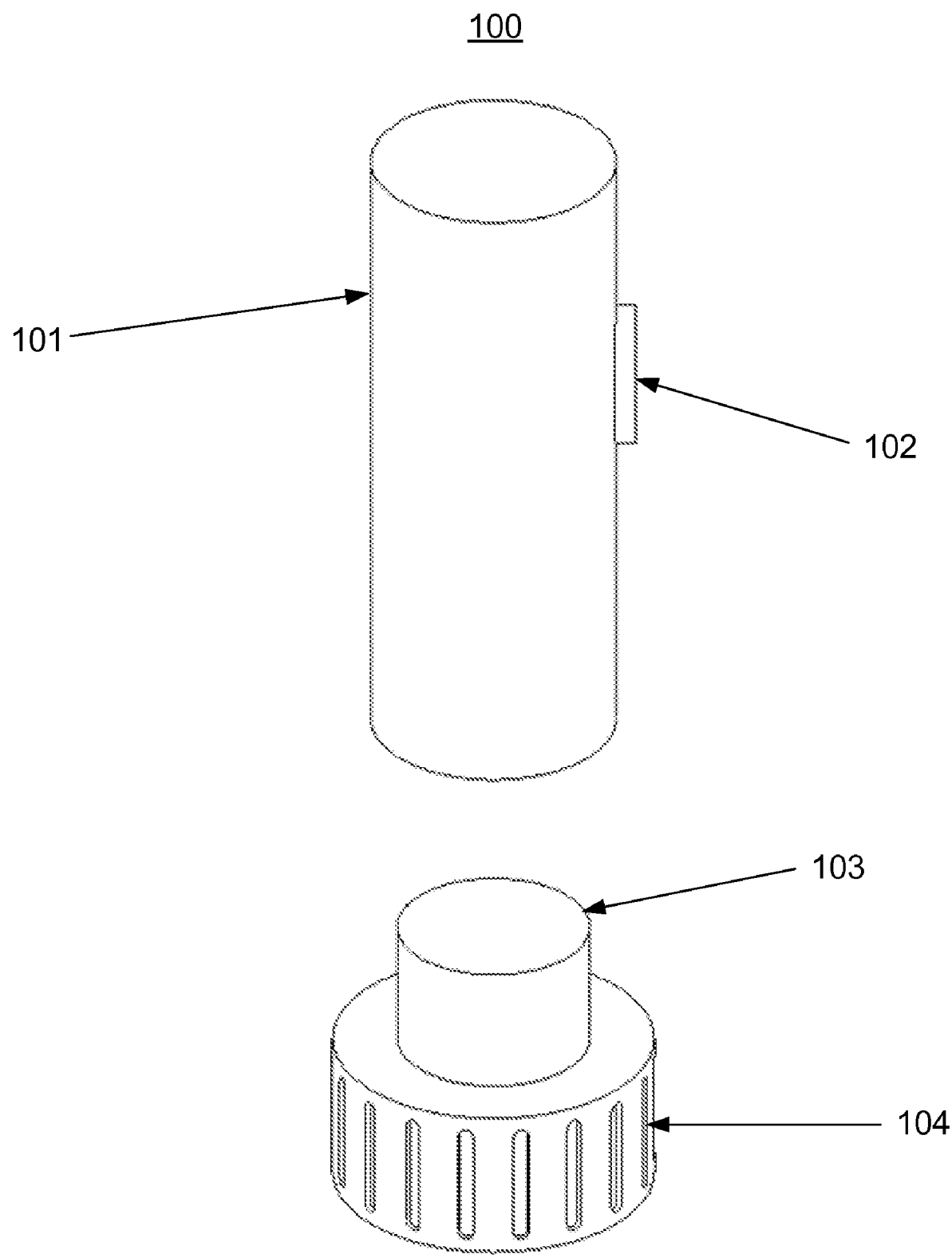
FIG. 1-*a* is a diagram illustrating a respiratory drug delivery system in open position, according to one embodiment of the present invention.
Figure 1B:
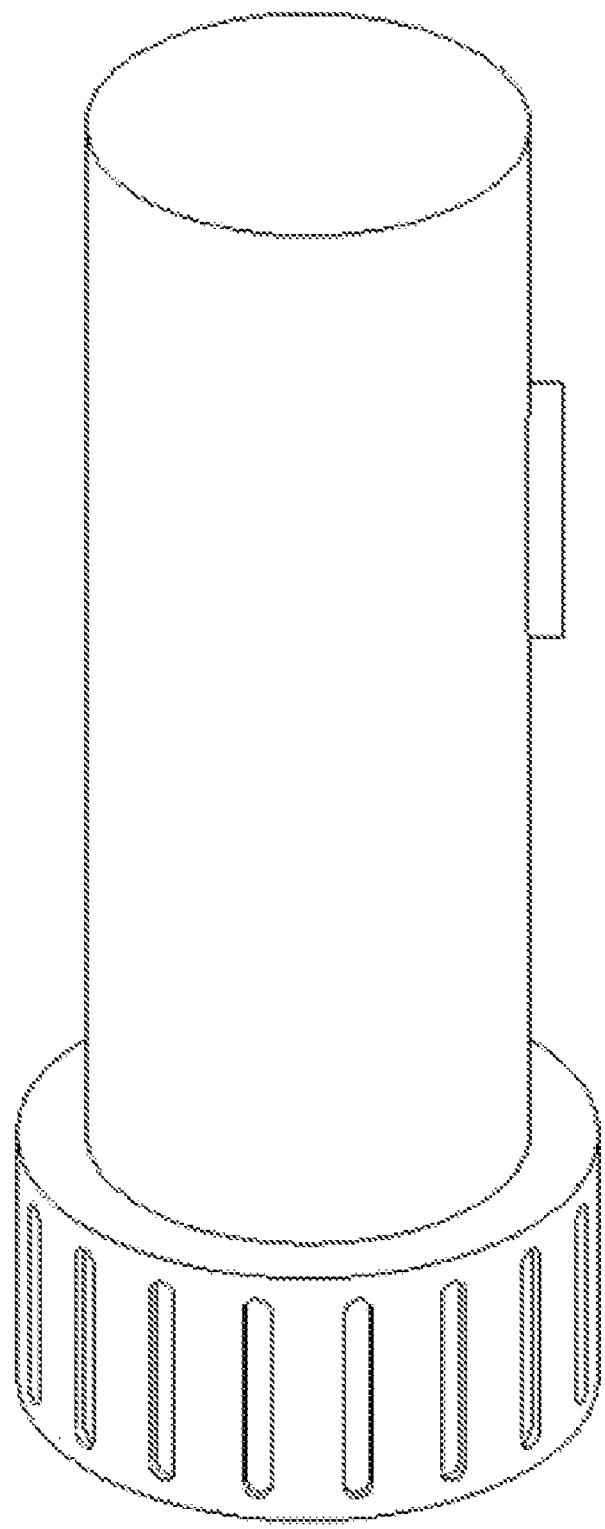
Figures 2A, 2B, 2C:
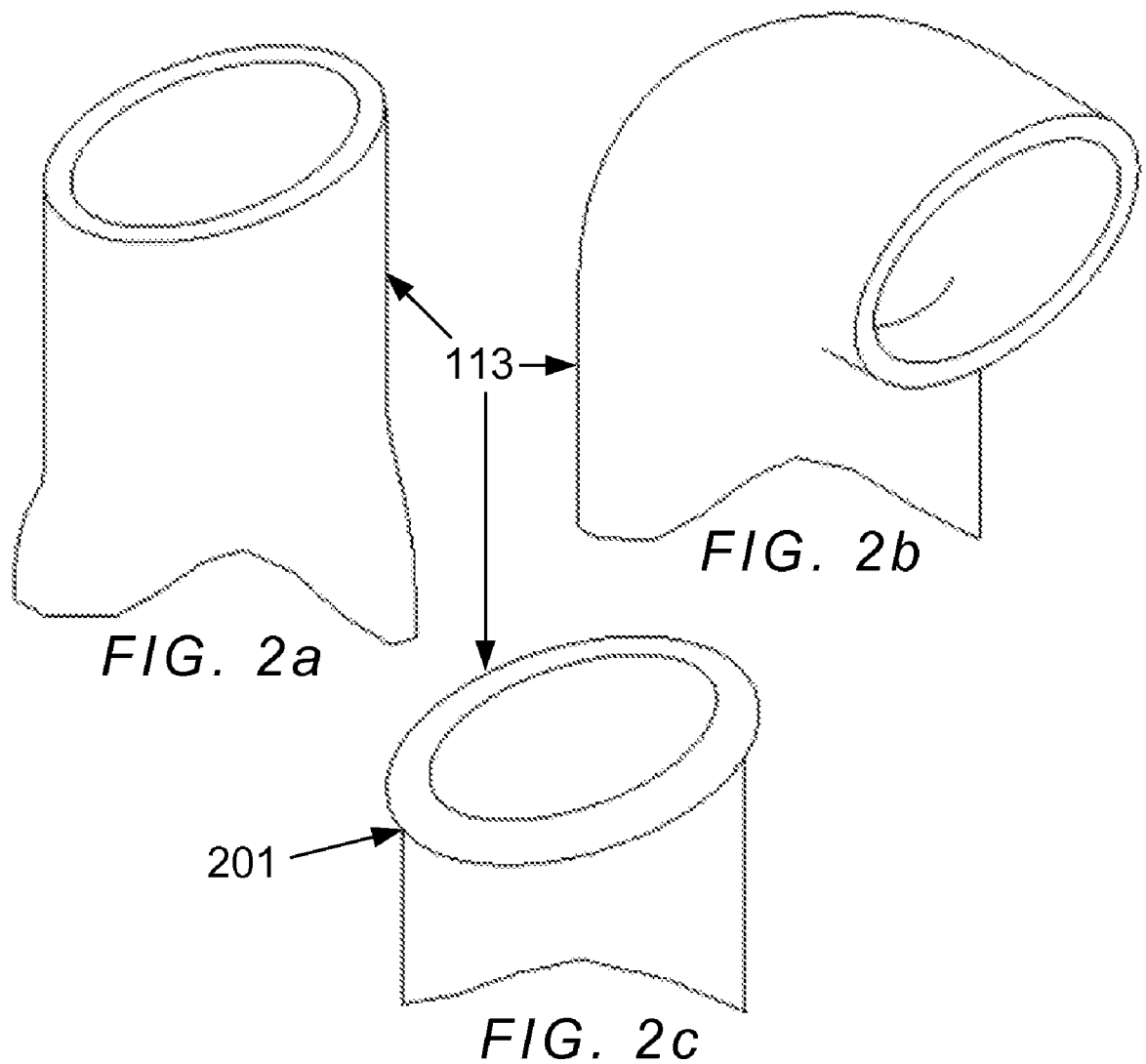
FIG. 2-*a* is a diagram illustrating tapered mouthpiece, according to one embodiments of the present invention.
Figure 2D:
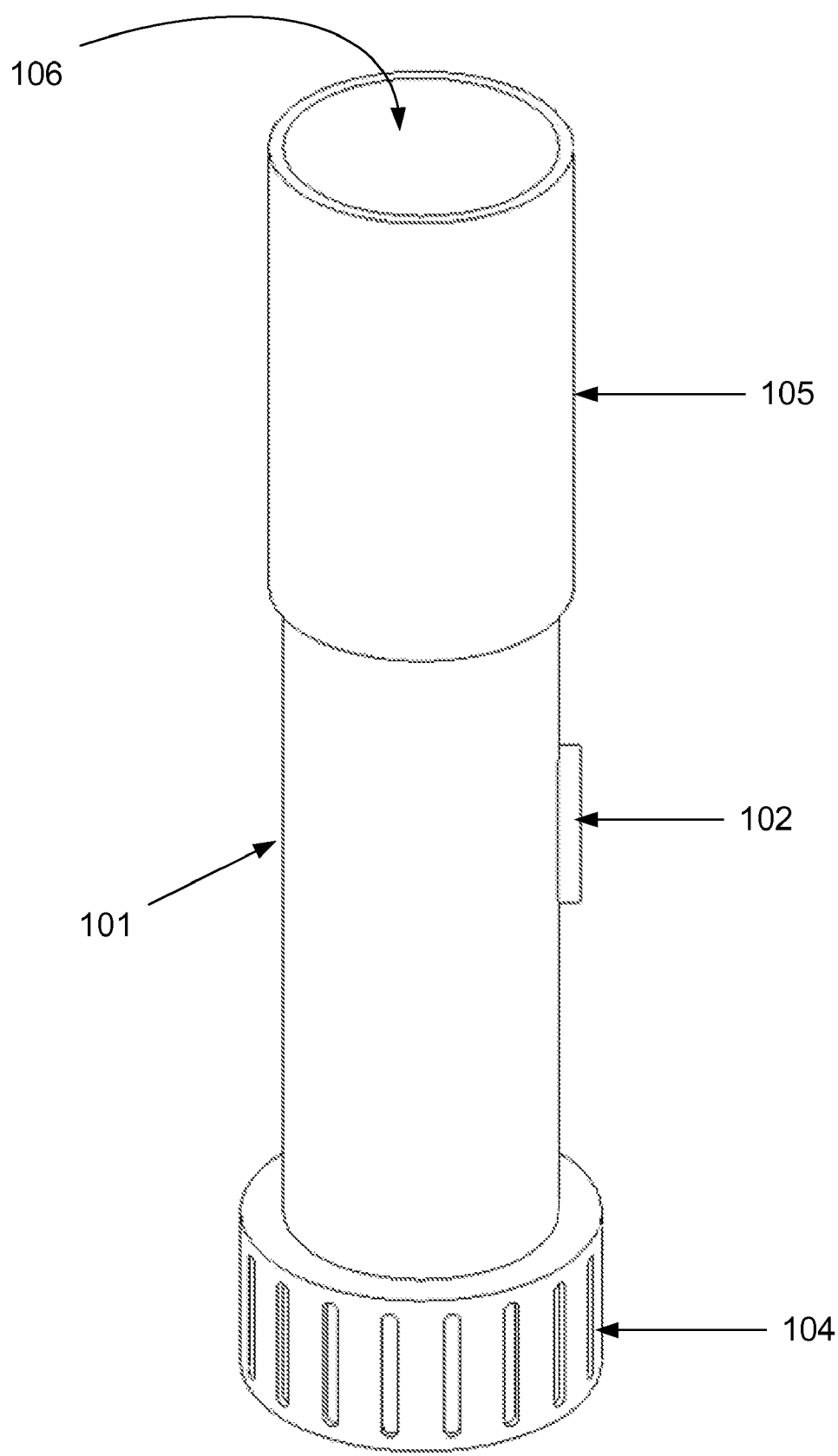

The invention provides systems, devices, and methods for respiratory drug delivery. In many aspects the invention relates to cartridges having drug and propellant compartments, or to distinct devices or methods that employ such cartridges.

By drug it is meant any drug or particles (such as Albuterol, Insulin, Budesonide, aromatherapy powder) or other substance for respiratory delivery. Thus, generally the invention provides systems and methods for aerosolizing a pharmaceutical formulation and delivering the pharmaceutical formulation to the respiratory tract of the user, and in particular to the lungs of the user. The pharmaceutical formulation may comprise powdered medicaments, liquid solutions or suspensions, and the like, and may include an active agent.

The active agent intended includes an agent, drug, compound, composition of matter or mixture thereof that provides some pharmacologic, often beneficial, effect. This includes foods, food supplements, nutrients, drugs, vaccines, vitamins, and other-beneficial agents. As used herein, the terms further include any physiologically or pharmacologically active substance that produces a localized or systemic effect in a patient. An active agent for incorporation in a pharmaceutical formulation may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically. The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof. Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense and inhibitory RNA. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients that are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation. Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperatures (Tg) above about 35° C., preferably above about 40° C., more preferably above 45°, most preferably above about 55° C. Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility—enhancing peptide excipients include dimers, trimers, tetramers, and pentamers comprising one or more hydrophobic amino acid components such as those described above. Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers. The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-.beta.-cyclodextrin and sulfobutylether-.beta.-cyclodextr-in), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", $52^{nd}$ ed., Medical Economics, Montvale, N.J. (1998), both of which are incorporated herein by reference in their entireties.

The propellant used is generally intended to be air, stable gas, a combination of gases and/or materials, or other substance for aerosolizing a drug. For example, the propellant may be composed of oxygen, carbon dioxide, or nitrogen, or a combination of these gases in any proportion. Depending on the embodiment, propellant may reside in a compartment at a specific volume or pressure, or reside in a compartment unpressurized.

By aerosolize it is meant disperse as an aerosol, i.e. as a suspension of small particles (such as drug particles) in air, stable gas, a combination of gases and/or materials, or other substance. "Mass median diameter" or "MMD" is a measure of mean particle size, since the powders of the invention are generally polydisperse (i.e., consist of a range of particle sizes). MMD values are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction. In one version, the powdered formulation for use in the present invention includes a dry powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

By chaser is generally meant compressed air, stable gas, a combination of gases or materials, or other substance for providing improved drug deposition via secondary push or flow, optionally distinct from propellant.

By membrane it is meant any material for separating a first drug or propellant or chaser from a second drug or propellant or chaser, such as a single-layer or multi-layer plastic, or metallic material such as aluminum or other metallic foil, or Polyethyleneterephthalate (PET), or High Density Polyethylene (HDPE), or other material for said separating. Non-permeable or low permeability materials are preferred. It is envisioned that the membrane need not necessarily be of homogenous or uniform chemical composition or physical structure. For example, a membrane might be made up of a foil-laminate components, such as an interior layer polyester/PP/PE (0.003 inch) bound with an adhesive to a layer of nylon/polyester/PP/PE (0.001 inch), which is bound with another adhesive to an aluminum foil (0.00035 inch), another adhesive and optional inks for labeling, and an exterior layer polyester/PP/PE (0.0048 inch). A "common membrane" indicates an area of close physical proximity between the envelopes of different compartments. A common membrane is not limited to homogenous or uniform chemical composition or physical structure. It is envisioned, for example, that a common membrane may be obtained by joining two separately manufactured compartments via an adhesive. In this case, the common membrane would be made up of the two adjacent membranes and the adhesive.

Figures 1, 3A:
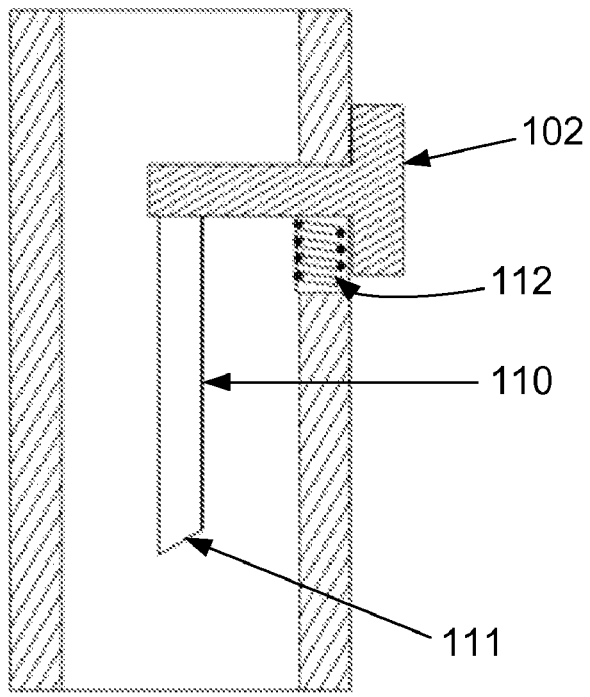

FIG. 1-*a* is a diagram illustrating a respiratory drug delivery system 100 in open position, according to one embodiment of the present invention. Respiratory drug delivery system 100 comprises a body 101 with a piercing trigger 102, and a cartridge 103. Cartridge 103 contains a drug, as well as a propellant for aerosolization of drug and respiratory delivery of drug to user. Optionally, cartridge 103 is mounted on or held by holder 104. FIG. 1-*b* illustrates respiratory drug delivery system 100 in closed position, according to one embodiment of the present invention.

Figures 2, 3A:
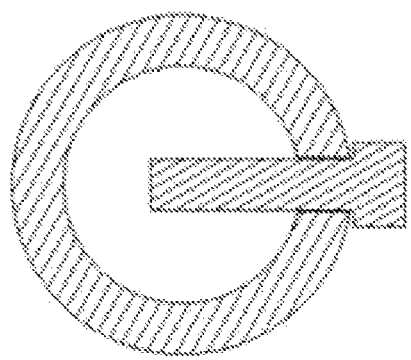
Figures 1, 3B:
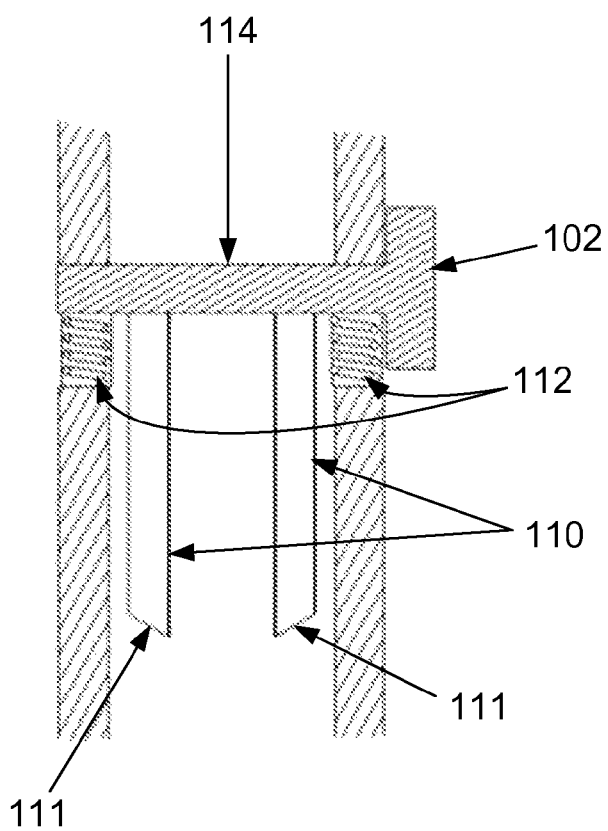
Figures 2, 3B:
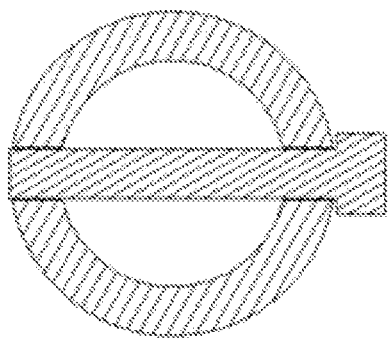
Figure 3C:
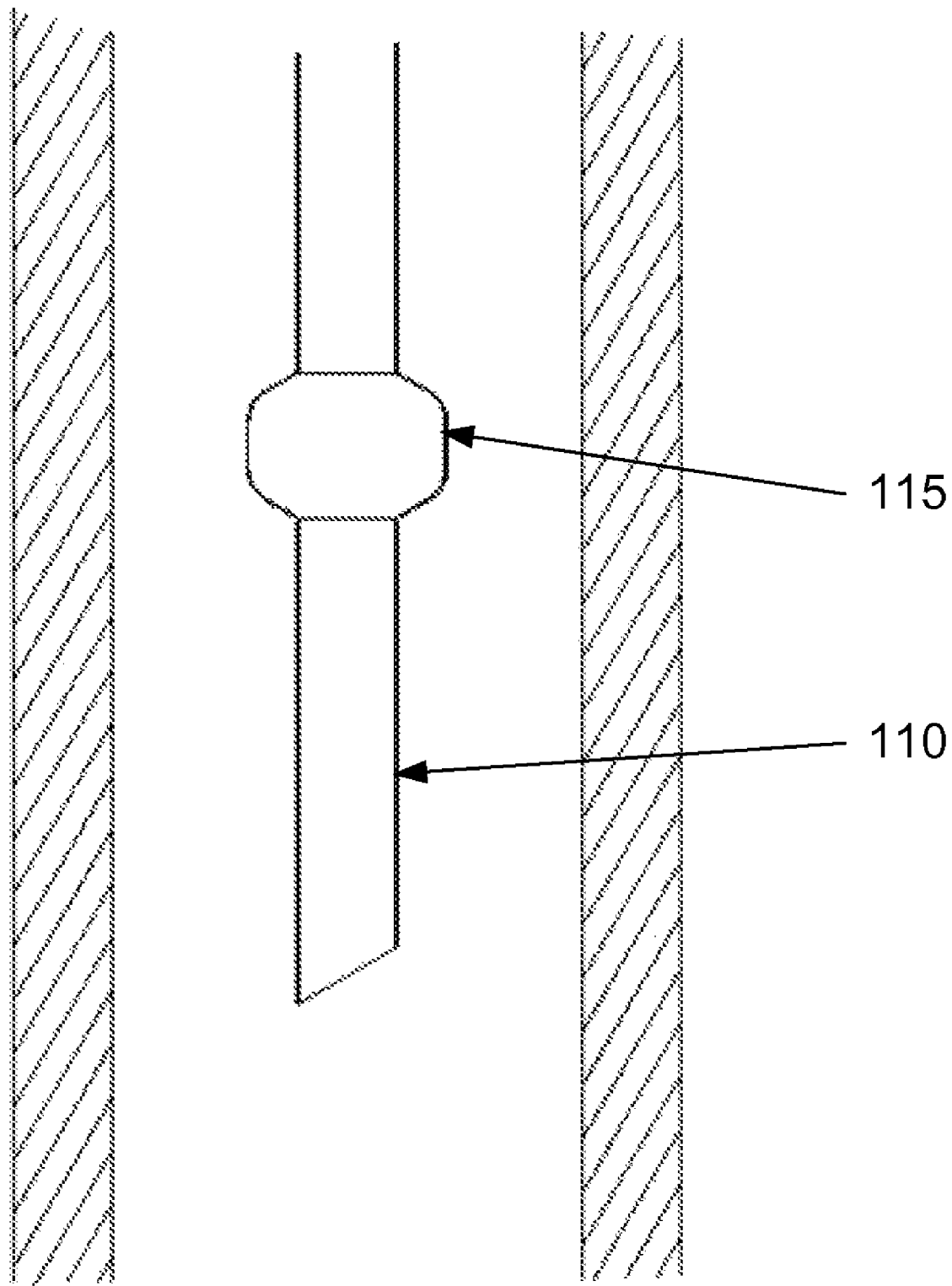
FIGS. 3-*a*1 and 3-*a*2 are diagrams illustrating cross-section of a single-tubing piercing mechanism, according to one embodiment of the present invention.
Figure 3D:
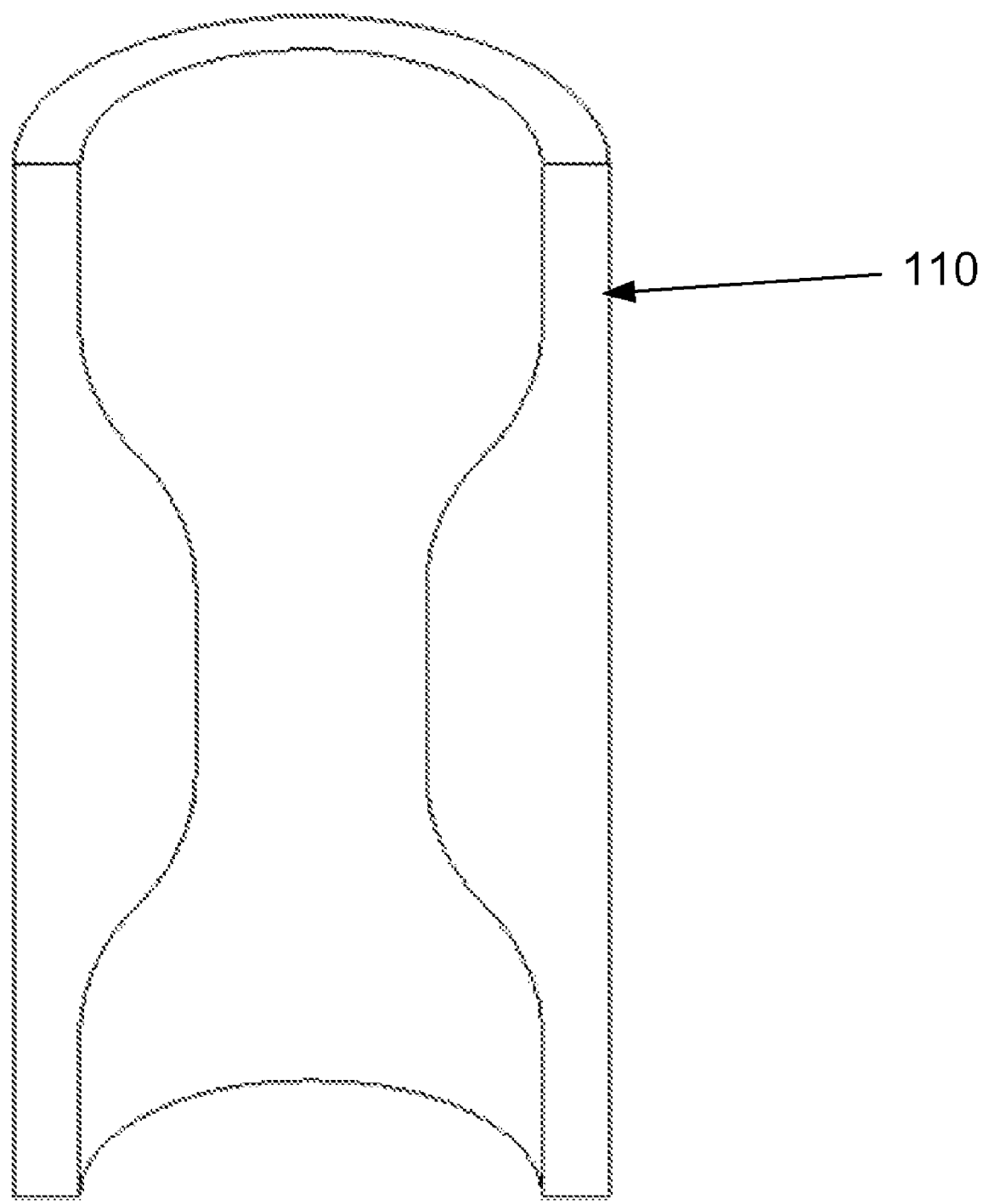
Figure 3E:
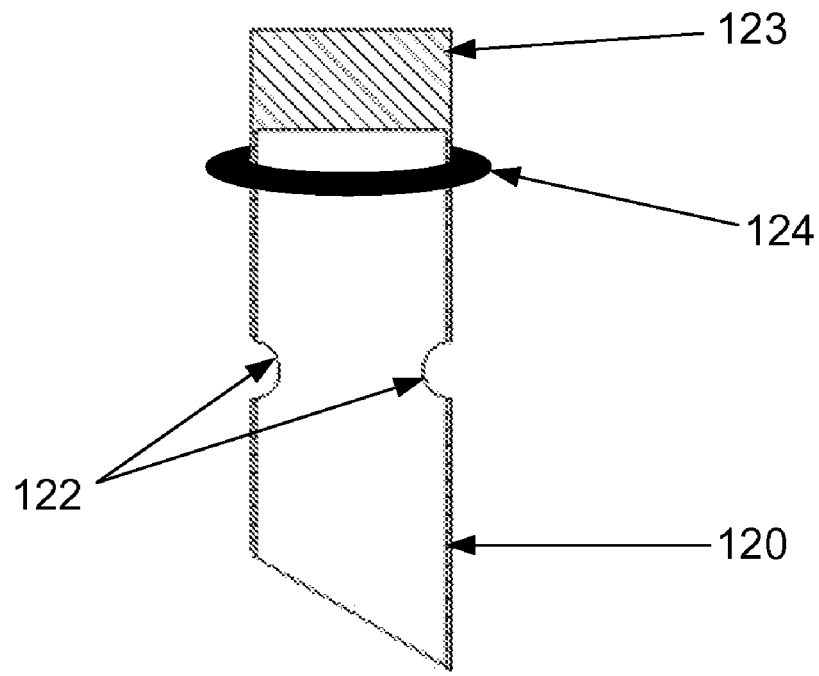
Figure 3F:
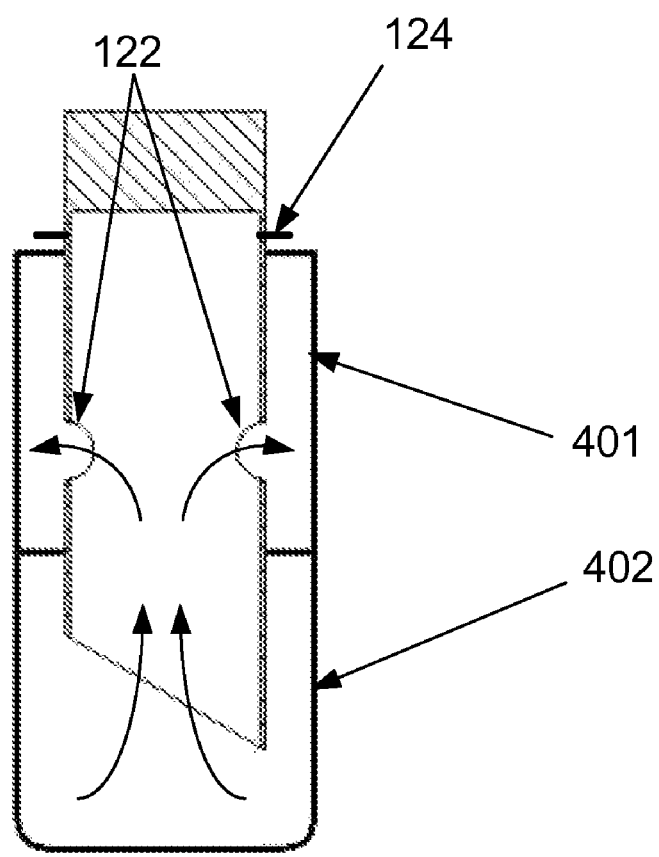
Figure 3H:
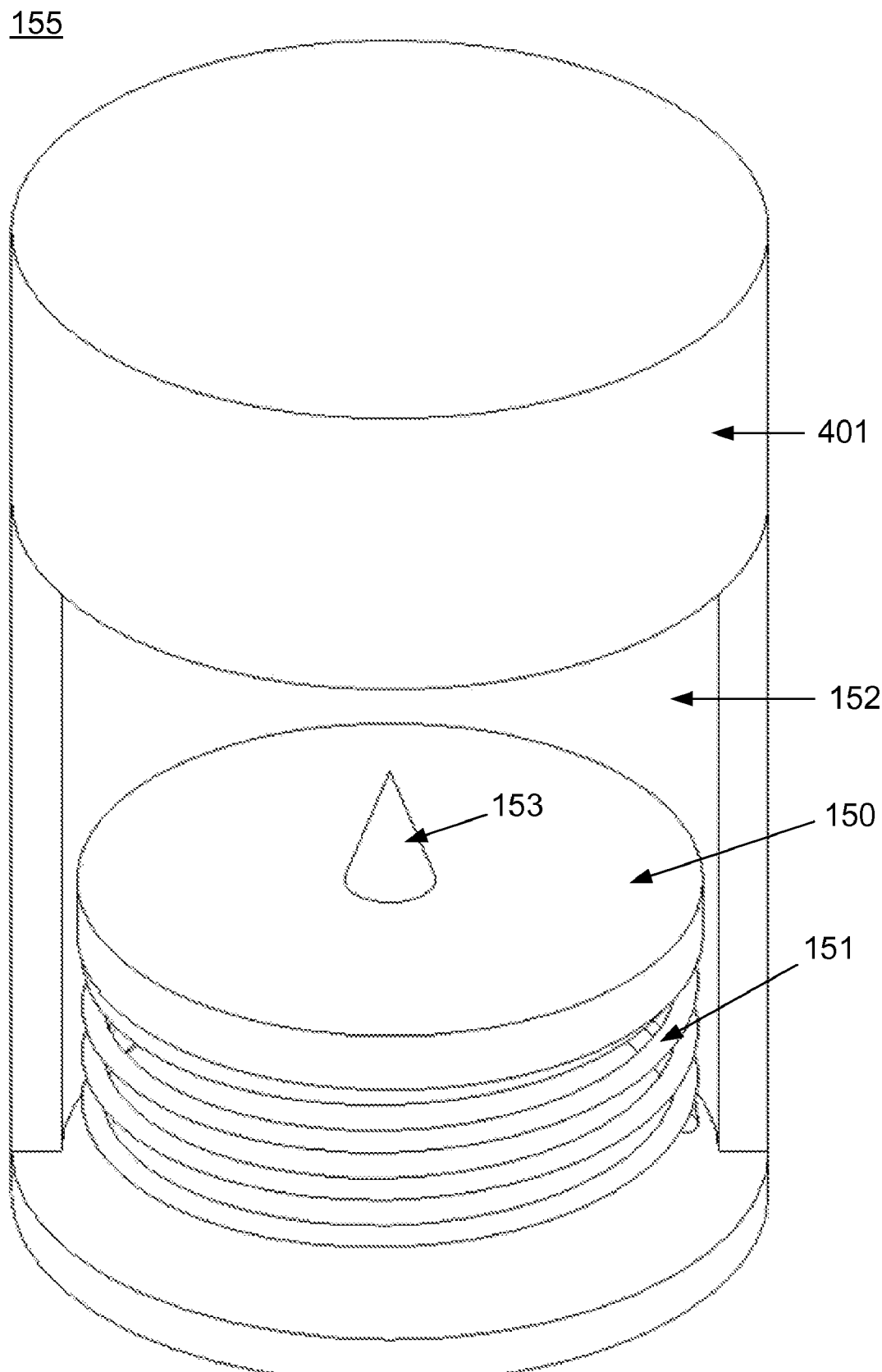
Figure 3I:
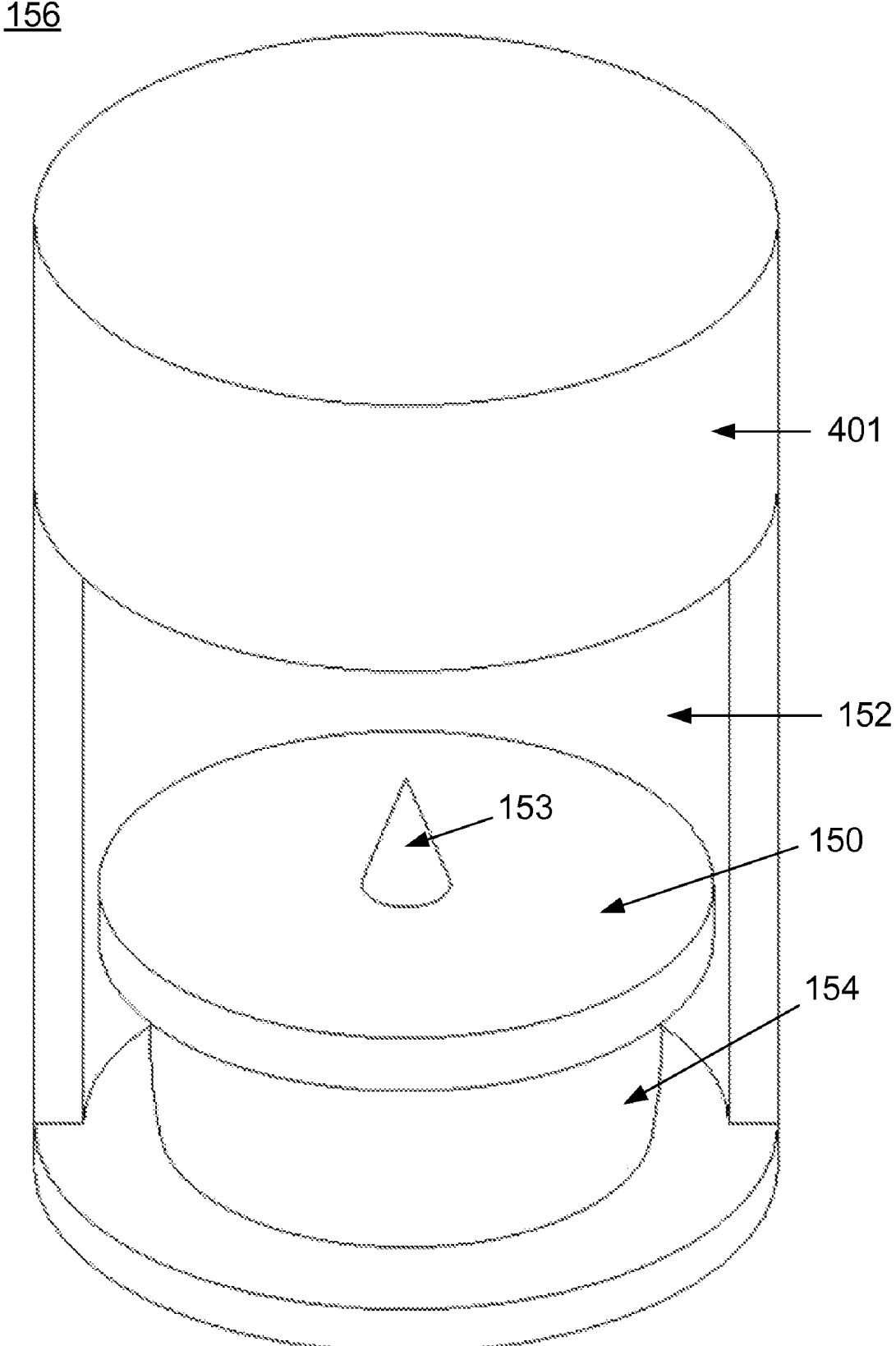
Figure 3J:
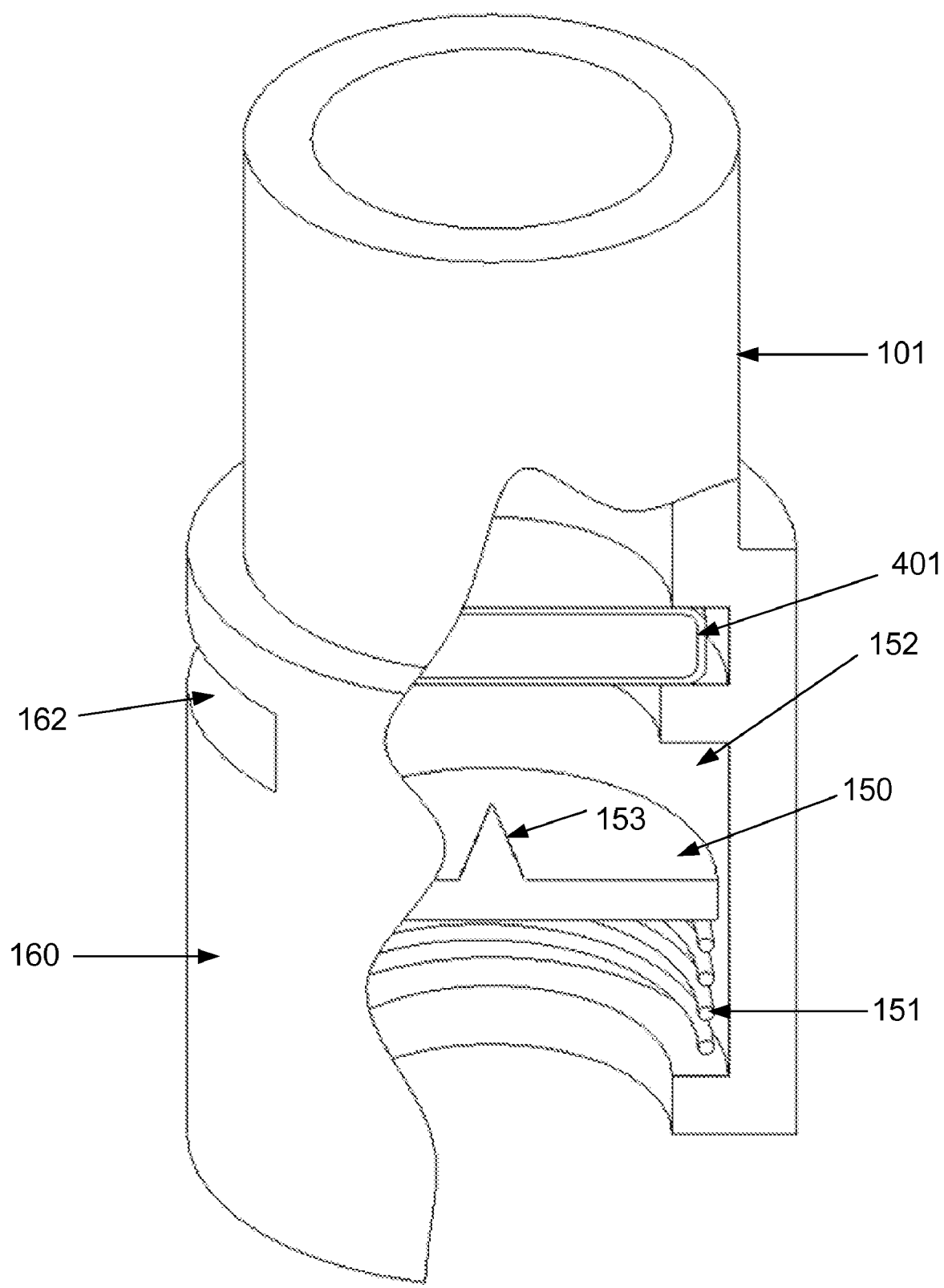
Figure 3K:
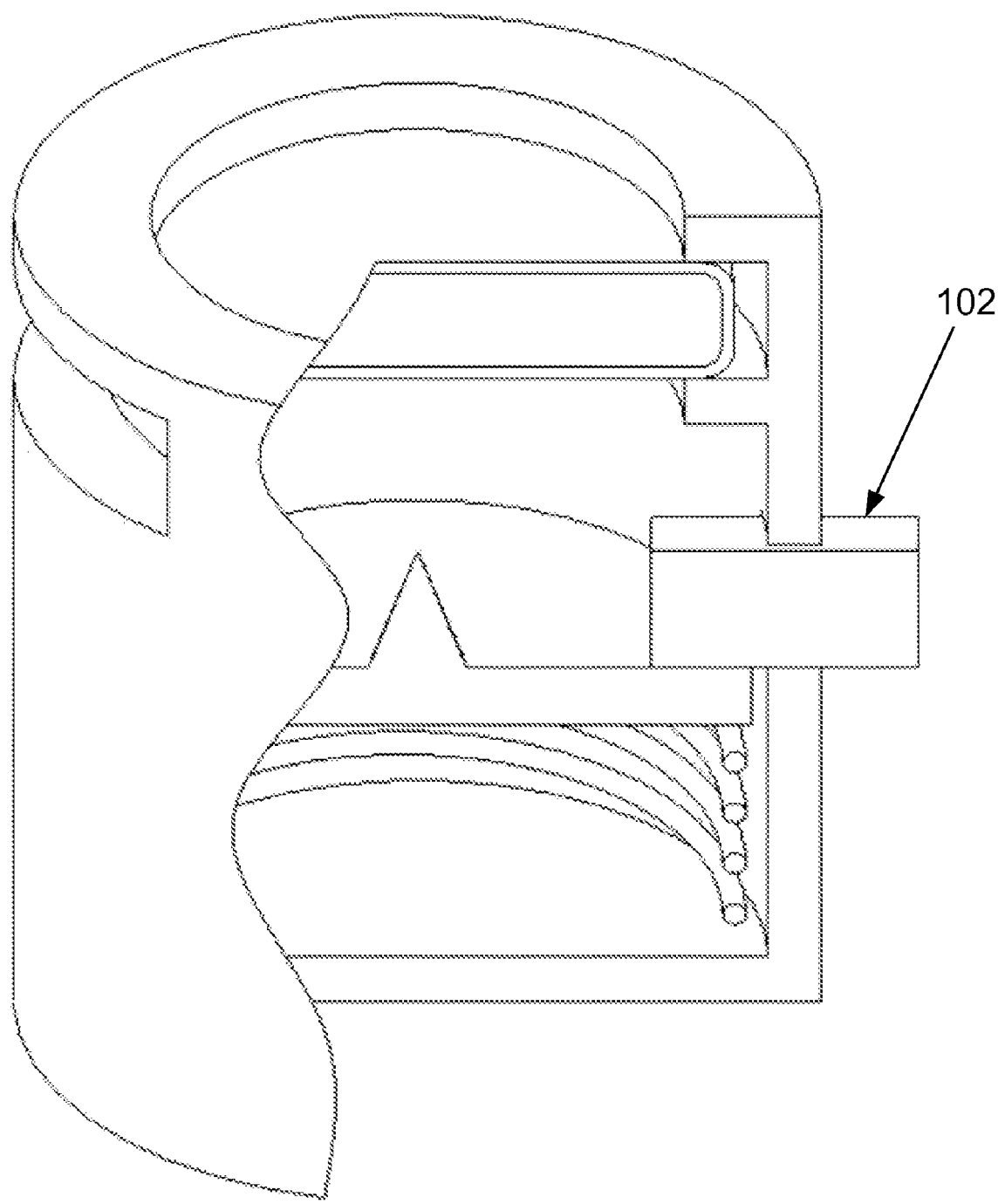

Body 101 comprises a mouthpiece 113 serving as inspiration opening for user. Mouthpiece 113 is the top end segment of body 101, or comprises a separate piece for coupling to top of body 101. Mouthpiece 113 is either a straight extension of body 101, or is shaped differently, for example as shown in FIG. 2-*a*, 2-*b* or 2-*c*. FIG. 2-*a* is a diagram illustrating a tapered mouthpiece, according to one embodiment of the present invention. FIG. 2-*b* is a diagram illustrating a bent mouthpiece, according to another embodiment of the present invention. FIG. 2-*c* is a diagram illustrating a grooved mouthpiece, according to another embodiment of the present invention. For example user can bite on groove 201 to position mouth relative to mouthpiece 113 and hold steady for facilitating maximal drug delivery. Positioning of mouthpiece 113 affects flow dynamics and path of aerosolized drug for improved drug delivery to lungs and drug deposition. Different mouthpiece 101 shapes can be chosen by user for optimum comfort.

FIG. 2-*d* is a diagram illustrating a respiratory drug delivery system with optional spacer 105, according to one embodiment of the present invention. Spacer 105 comprises a mouthpiece 113 serving as inspiration opening for user (analogous to the mouthpiece for body 101 described above) with mouthpiece 113 as the top end part of spacer 105 or comprising a separate piece for coupling to top of spacer 105, as shown in FIG. 2-*a*, 2-*b* or 2-*c*. Spacer 105 comprises a chamber 106 for storing an aerosolized drug prior to respiratory delivery. When using a spacer 105, mouthpiece 113 comprises a mechanism for holding the aerosolized drug within chamber 106 until user releases held aerosolized drug for respiratory delivery. In one embodiment, mouthpiece 113 comprises a lid and the user releases held aerosolized drug by activating a handle coupled to the lid. In another embodiment, the user releases held aerosolized drug by twisting the mouthpiece 113 to create an opening, wherein spacer 105 and mouthpiece 113 each comprise an opening at their common plane of contact, which openings can be either aligned for allowing a pathway for the aerosolized drug to travel from chamber 106 through mouthpiece 113, or misaligned for prohibiting travel of aerosolized drug.

FIGS. 3-*a*1 and 3-*a*2 are diagrams illustrating cross-section of a single-tubing piercing mechanism, according to one embodiment of the present invention. Pierce tubing 110 comprises opening 111. Spring 112 pushes pierce tubing 110 away from cartridge 103. Activating piercing trigger 102 moves pierce tubing 110 towards cartridge 103 for piercing cartridge 103. Pierce tubing 110 comprises plastic, metal, or other durable or disposable material. FIG. 3-*a*2 illustrates a top view of the single piercing mechanism.

Optionally, piercing mechanism and/or piercing trigger 102 are electrically powered, using a disposable or rechargeable battery or other power source.

FIG. 3-*b*1 and 3-*b*2 are diagrams illustrating a cross-section of a multi-tubing piercing mechanism, according to one embodiment of the present invention. Two pierce tubings 110 are shown in the figure as examples. Other embodiments with additional pierce tubings 110 are analogous. The double-piercing mechanism depicted in FIG. 3-*b*1 comprises two pierce tubings 110, pushed away from cartridge 103 by springs 112. Pierce tubings 110 comprise openings 111, and are mounted on a ring shaped support structure 114. Pierce tubings 110 may be of different lengths, advantageously resulting in staggered cartridge piercing times (i.e. temporally offset or occurring sequentially) when trigger 102 is activated, for staggered drug aerosolization or drug delivery. FIG. 3-*b*2 illustrates a top view of the double-piercing mechanism.

FIG. 3-*c* is a diagram illustrating a cross-section of a bumped-piercing mechanism, according to one embodiment of the present invention. Pierce tubing 110 comprises bump 115 for staged aerosolization. Upon engaging trigger 102, the resistance of bump 115 accompanying the passing of bump 115 through a membrane of cartridge 103 indicates to the user that the membrane has been pierced. The first instance of resistance indicates piercing of the topmost membrane, the second instance of resistance indicating piercing of the membrane following the topmost membrane, and so forth. The user may thereby deduce when a drug is aerosolized and/or delivered and/or when to initiate a chaser. In addition, some drugs have no taste, making it difficult for a user to know whether the drug has been delivered or not, and bump 115 can indicate drug delivery in such cases.

FIG. 3-*d* is a diagram illustrating necked interior cross-section of pierce tubing 110, according to one embodiment of the present invention. The necked design improves velocity of propellant (released from propellant compartment) through pierce tubing 110 for achieving improved propellant flow (for example sonic or hyper-sonic flow) for improved mixing of drug with propellant or for improved mixing of different drugs coming from different drug compartments. Alternatively, pierce tubing 110 does not have necked interior cross-section, but has simple cylindrical interior.

FIG. 3-e is a diagram illustrating detail of pierce head, according to one embodiment of the present invention. The head 120 of pierce tubing 110 is hollow with openings 122 on the side, and cross-section 123 is closed to prevent propellant flow beyond cross-section 123. Stopper ring 124 stops piercing movement of pierce tubing 110 through membrane 403 for proper positioning of openings 122 and for preventing openings 122 to cross membrane 403 into the propellant compartment. Stopper ring 124 may also serve as a seal, preventing leakage of drug or aerosolized drug from drug compartment 401 into body 101.

FIG. 3-f is a diagram showing simulation of air and drug flow through pierce tubing 110, according to one embodiment of the present invention. When pierce head 120 of pierce tubing 110 pierces propellant compartment 402, the pressure in propellant compartment 402 causes the propellant to flow through pierce head 120 and out through openings 122 into the drug compartment 401. This provides mixing of propellant with drug and/or de-agglomeration of drug, for increased rate and/or efficiency of drug delivery. Upon release of piercing trigger 102, pierce tubing 110 retracts from propellant compartment 402 and from drug compartment 401, providing an opening for the flow of aerosolized drug into body 101 and to user.

In an alternative embodiment, pierce tubing 110 is hollow over its entire length, with an opening at the top of pierce tubing 110. Pierce tubing head 120 pierces drug compartment 401, collecting into the hollow pierce tubing 110 an amount of the drug in drug compartment 401. Subsequent piercing of propellant compartment 402 causes the propellant to flow through pierce tubing 110, and mix with and/or aerosolize the drug collected in pierce tubing 110. Propellant and drug then travel out through the opening at the top of pierce tubing 110 and into body 101 for respiratory delivery. Pierce tubing 110 may comprise a large diameter for collecting sufficient amount of drug into the hollow pierce tubing 110 (for example an external diameter close to the internal diameter of the pierced compartments).

FIGS. 3-*g*1, 3-*g*2 and 3-*g*3 are diagrams illustrating a pierce tip of the pierce head and corresponding membrane puncture, according to one embodiment of the present invention. FIG. 3-*g*1 shows pierce head 120 having pierce tip 125 with cross-section as shown in FIG. 3-*g*2. Upon piercing a membrane 403, pierce tip 125 produces pie like puncture and opening as shown, with flaps opening away as forced by outward flow of propellant or aerosolized drug. Alternatively, pierce tip 125 comprises pierce head 125 with tapered opening similar in shape to a syringe needle opening, producing a circular or round cut in membrane 403 opening away as forced by outward flow of propellant or aerosolized drug.

FIG. 3-*h* is a diagram illustrating a disposable cartridge 155 with spring-loaded plunger mechanism, according to one embodiment of the present invention. Plunger 150 is mounted on loaded spring 151 at the bottom of chamber 152. Plunger 150 has pierce head 153 for piercing drug compartment 401. Chamber 152 contains a propellant, wherein the propellant may or may not be pressurized. After releasing loaded spring 151 (for example by activating a release lever coupled to piercing trigger 102, or by activating a trigger mounted on the disposable cartridge 155 itself, or by using another mechanism for releasing loaded spring 151), spring 151 thrusts plunger 150 upwards, piercing drug compartment 401 with pierce head 153, thrusting propellant into drug compartment 401 and aerosolizing drug for respiratory delivery.

FIG. 3-*i* is a diagram illustrating a disposable cartridge 156 with compressed-elastomer plunger mechanism, according to one embodiment of the present invention. Plunger 150 is mounted on compressed elastomer 154 at the bottom of chamber 152. Plunger 150 has pierce head 153 for piercing drug compartment 401. Chamber 152 contains a propellant, wherein the propellant may or may not be pressurized. After releasing compressed elastomer 154 (for example by activating a release lever coupled to piercing trigger 102, or by activating a trigger mounted on the disposable cartridge 156 itself, or by using another mechanism for releasing compressed elastomer 154), compressed elastomer 154 thrusts plunger 150 upwards, piercing drug compartment 401 with pierce head 153, thrusting propellant into drug compartment 401 and aerosolizing drug for respiratory delivery.

FIG. 3-*j* is a diagram illustrating a reusable cartridge 160 with spring-loaded plunger mechanism, according to one embodiment of the present invention. Reusable cartridge 160 is permanently coupled to body 101 and has slot 162 for inserting a drug compartment 401. Plunger 150 is mounted on loaded spring 151 at the bottom of chamber 152. Plunger 150 has pierce head 153 for piercing inserted drug compartment 401. Chamber 152 contains a propellant, wherein the propellant may or may not be pressurized. After releasing loaded spring 151 (for example by activating a release lever coupled to piercing trigger 102, or by activating a trigger mounted on the reusable cartridge 160 itself, or by using another mechanism for releasing loaded spring 151), spring 151 thrusts plunger 150 upwards, piercing drug compartment 401 with pierce head 153, thrusting propellant into drug compartment 401 and aerosolizing drug for respiratory delivery. Alternatively, reusable cartridge 160 is not permanently coupled to body 101, but allows coupling of body 101 onto top of cartridge 160 when in use and allows for removal of body 101 from cartridge 160 when not in use, as shown in FIG. 3-*k*.

FIG. 4-*a* is a diagram illustrating a drug cartridge 103 with one drug compartment 401 and one propellant compartment 402. Compartments 401 and 402 are separated by membrane 403. Compartment 401 contains a drug, such as Albuterol, Budesonide, Insulin, or other powdered drug for respiratory delivery. Compartment 402 contains a propellant. Propellant in compartment 402 is pressurized, for example at a pressure of 1 psi to 50 psi. A pressure below 1 psi or above 50 psi may be used, for example for a user with low inspiratory flow rate such as a pediatric patient or a cystic fibrosis patient, or for a user with high inspiratory flow rate such as an athlete, or for a user with low or high lung capacity, for providing comfort and maximal drug deposition. Cartridge 103 material comprises single-layer or multi-layer plastic or metallic material, or other material for containing drug and/or propellant.

The propellant compartment may be enveloped by any suitable membrane material or combination of materials, such as a single-layer or multi-layer plastic, or metallic material such as aluminum or other metallic foil, or Polyethyleneterephthalate (PET), or High Density Polyethylene (HDPE), etc. The compartment may be formed by any suitable method, such as the blow-fill-seal process. Propellant gas can be introduced into the compartment by the blow fill seal method before sealing. To join a drug compartment or blister to the propellant compartment, the two compartments may be prepared separately and later glued together along a common surface. Any suitable adhesives may be used to form the common surface. Typical adhesive components are aromatic C5 hydrocarbon resin, polymeric hindered phenol (anti-oxidant), diastearyl pentaerythrotol diphosphate (anti-oxidant), styrene-isopropene-styrene block polymer, naphthenic oil, and liquid C5 hydrocarbon resin.

Figure 4A:
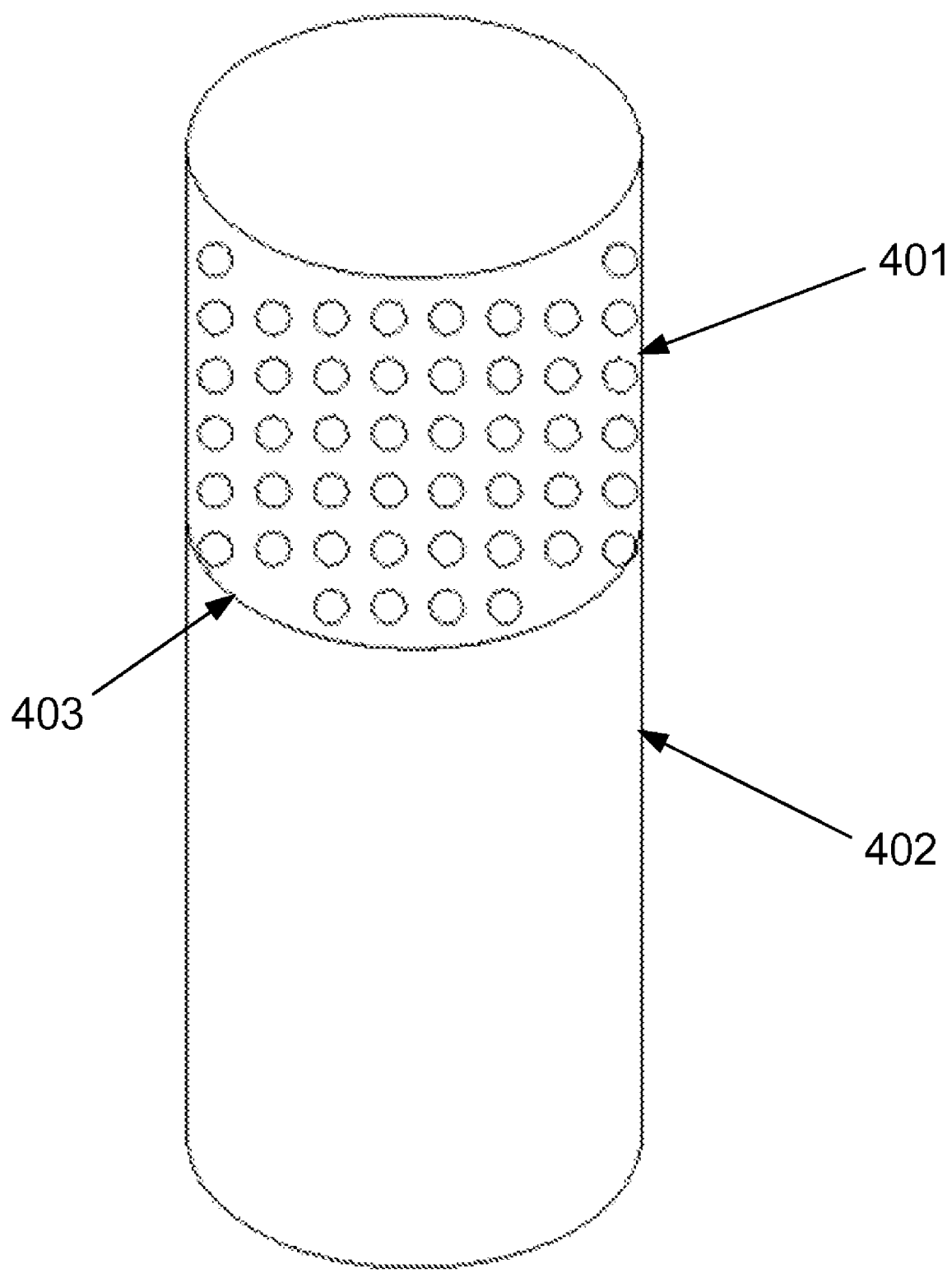
FIG. 4-*a* is a diagram illustrating a drug cartridge with one drug compartment and one gas compartment, according to one embodiment of the present invention.
Figure 4B:
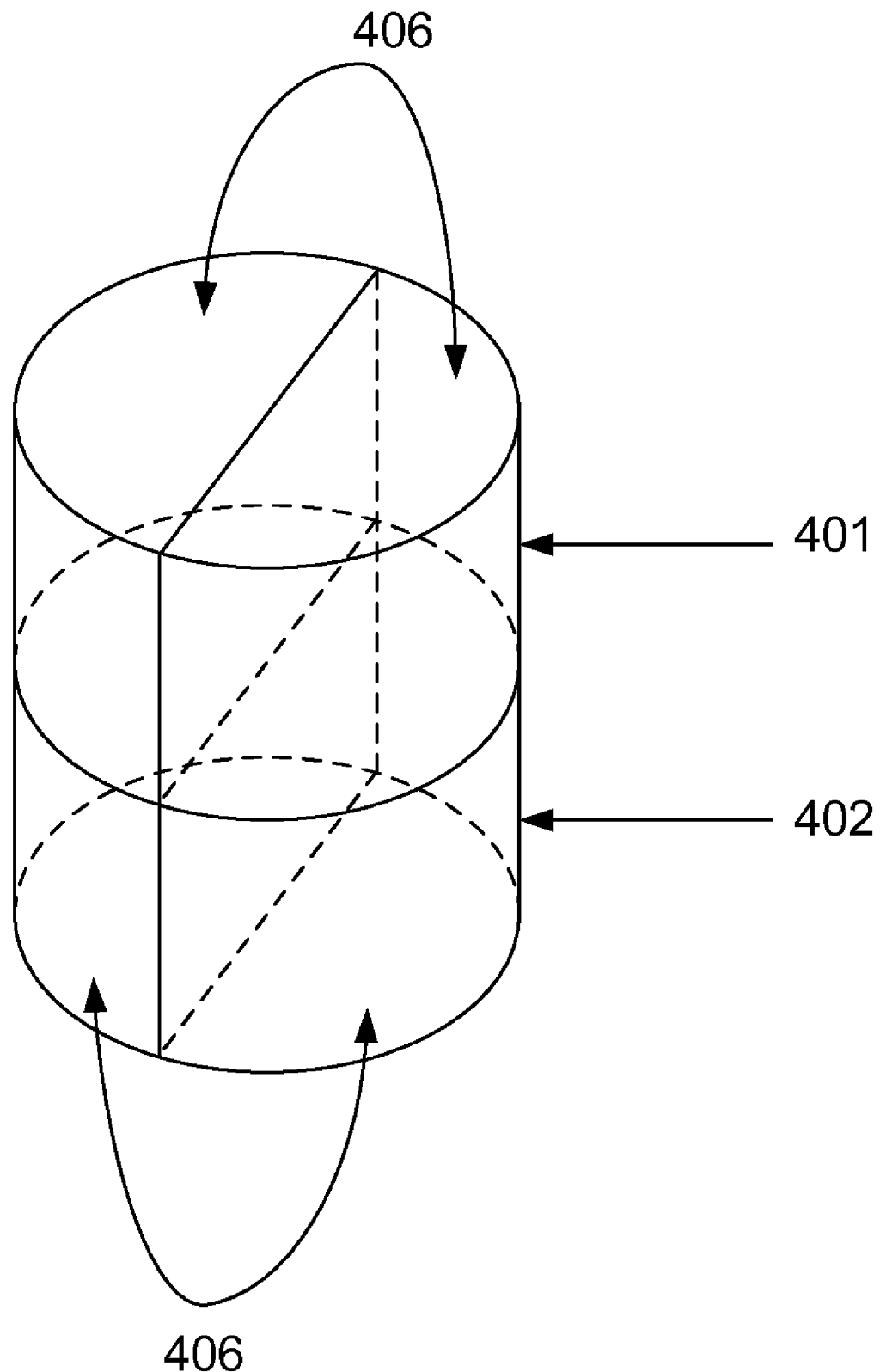
Figure 4C:
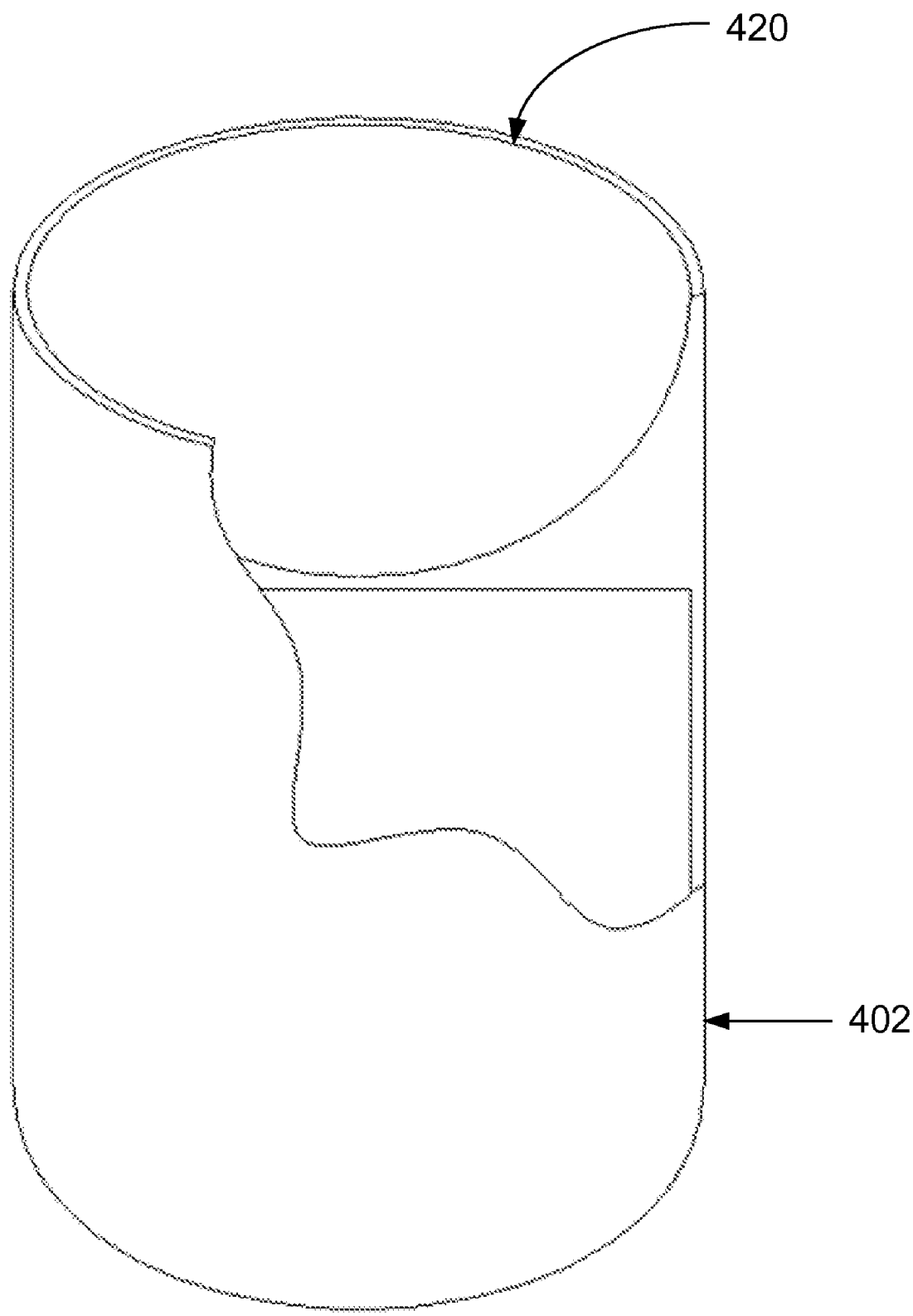
Figure 4D:
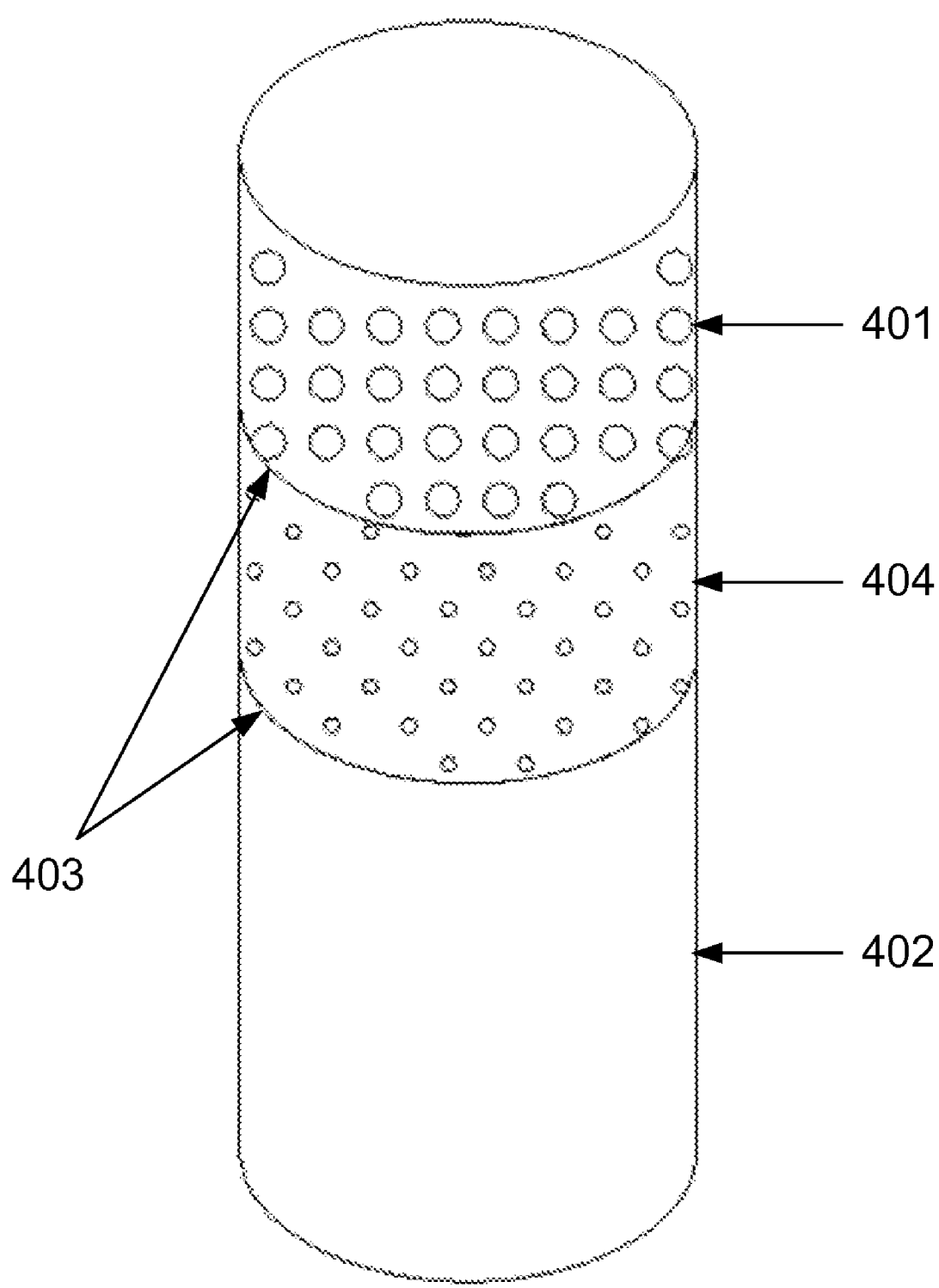
Figure 4E:
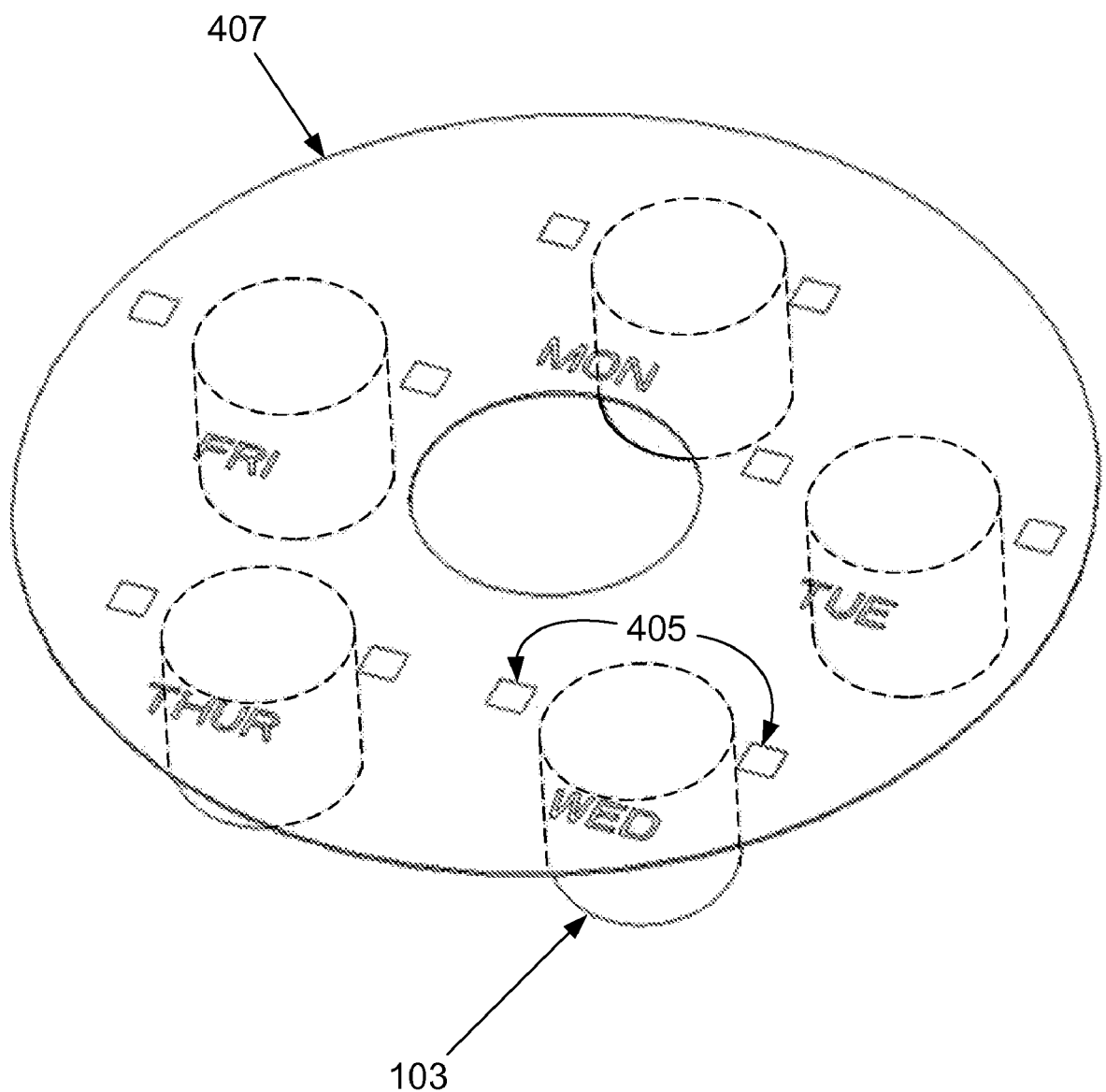
Figure 4F:
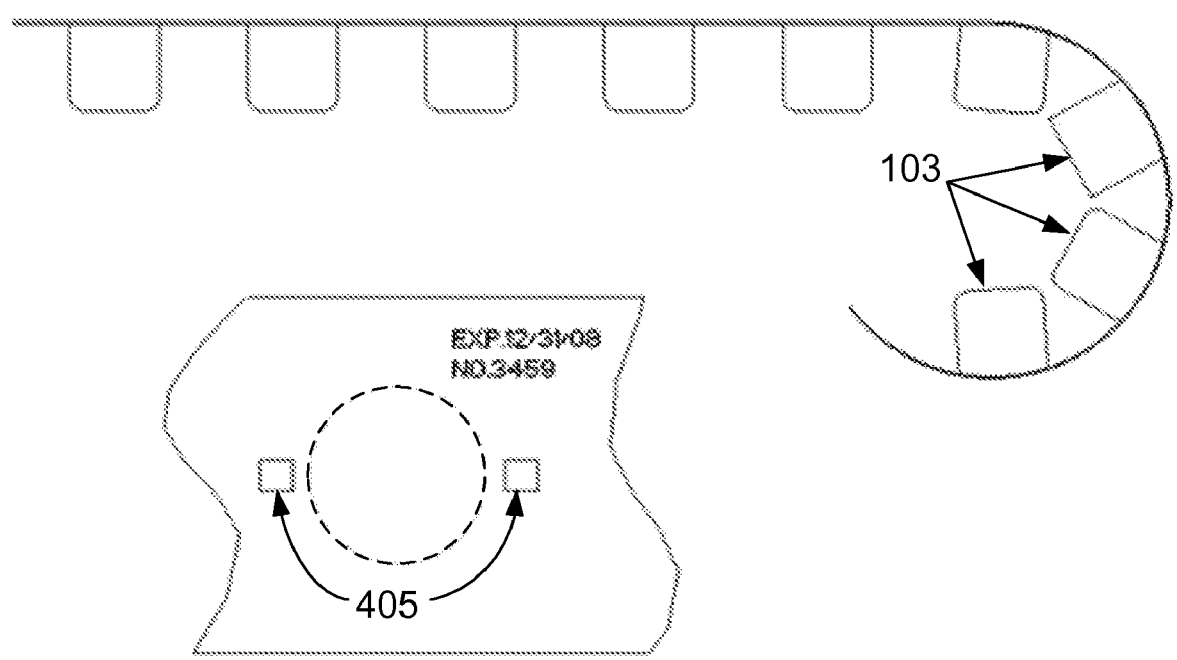
Figure 5A:
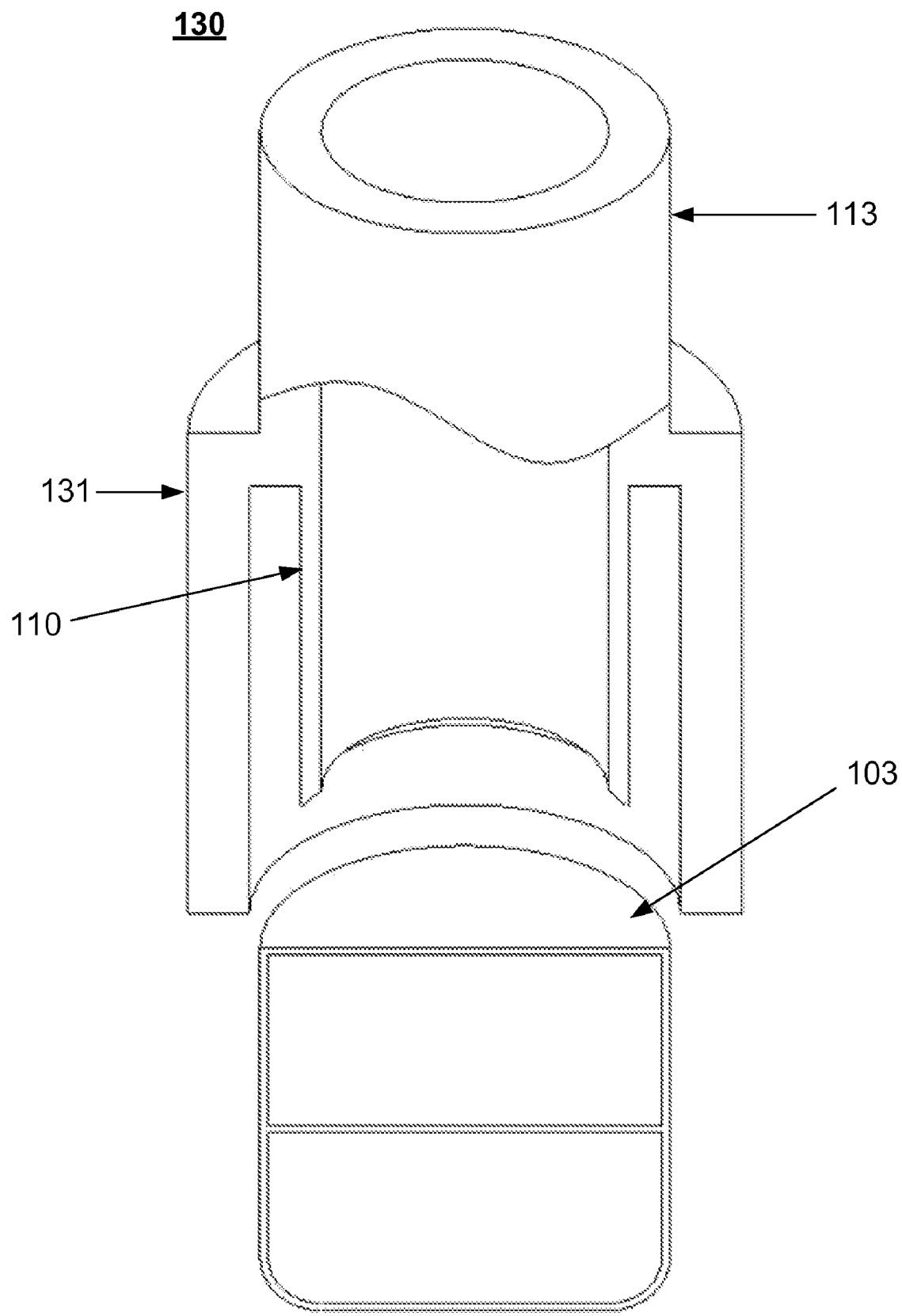
FIG. 5-*a* is a diagram illustrating a micro-version of the respiratory drug delivery system, according to one embodiment of the present invention.
Figure 5B:
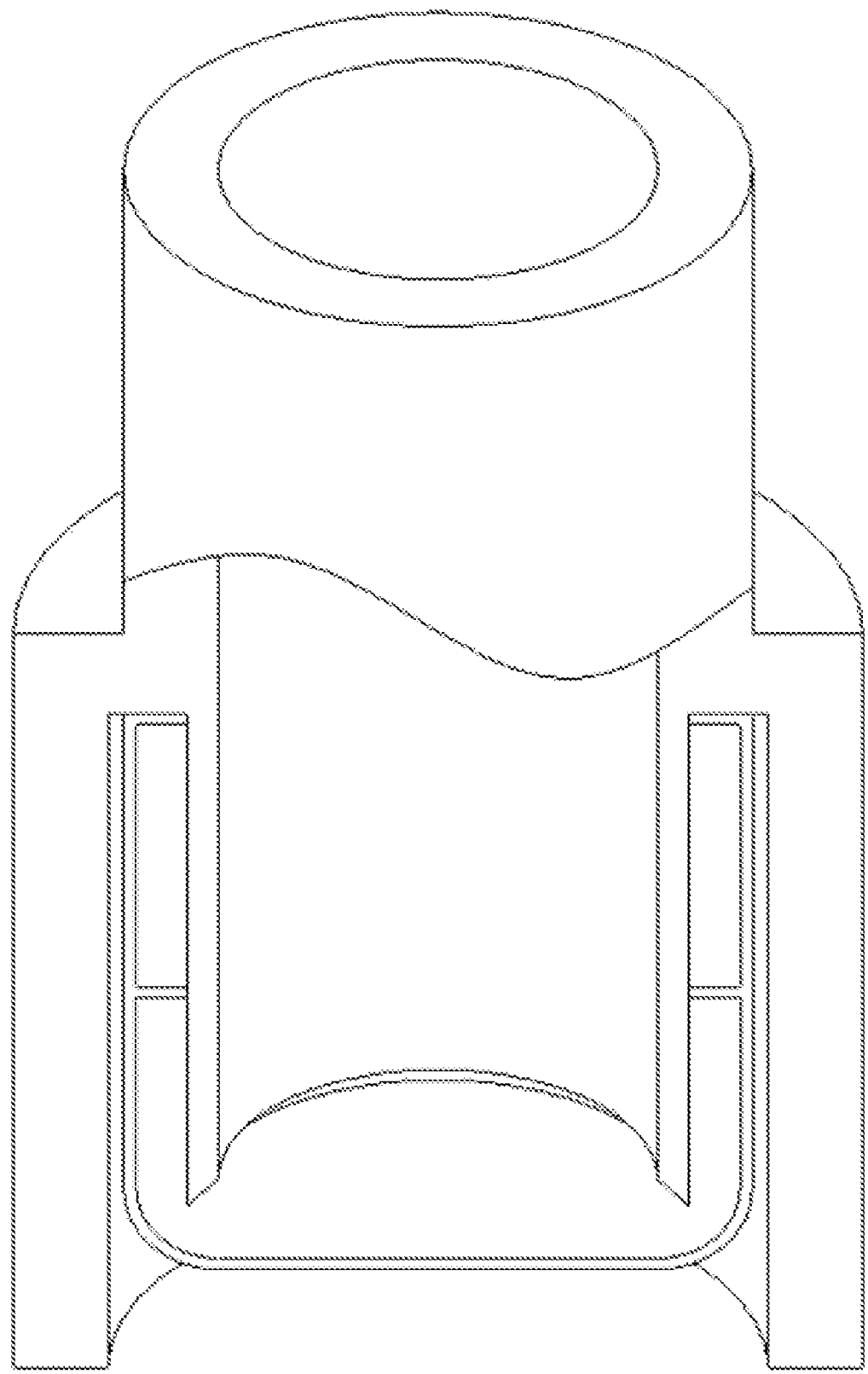
Figure 6:
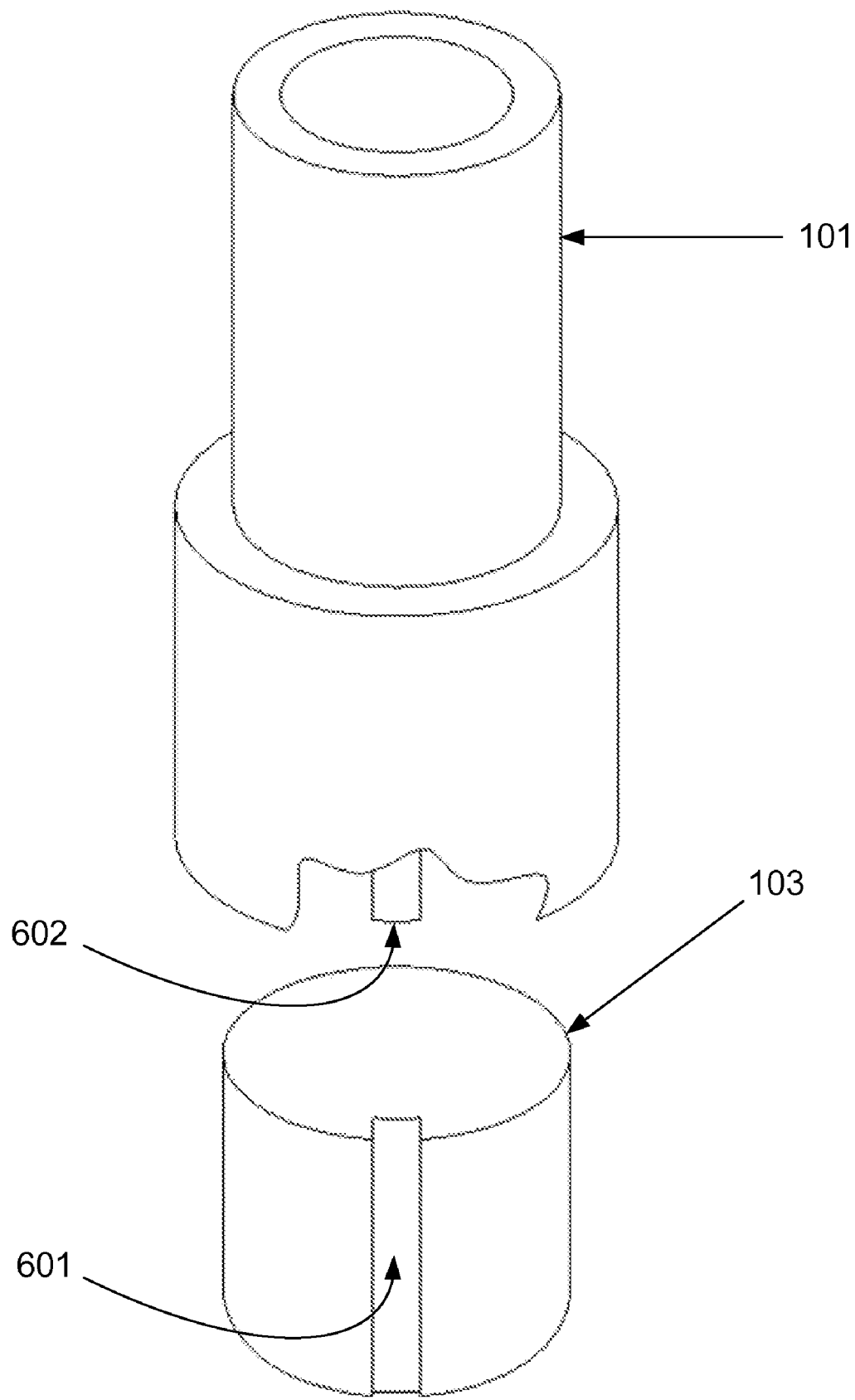
FIG. 6 is a diagram illustrating optional locators on drug cartridge, according to one embodiment of the present invention.
Figure 8:
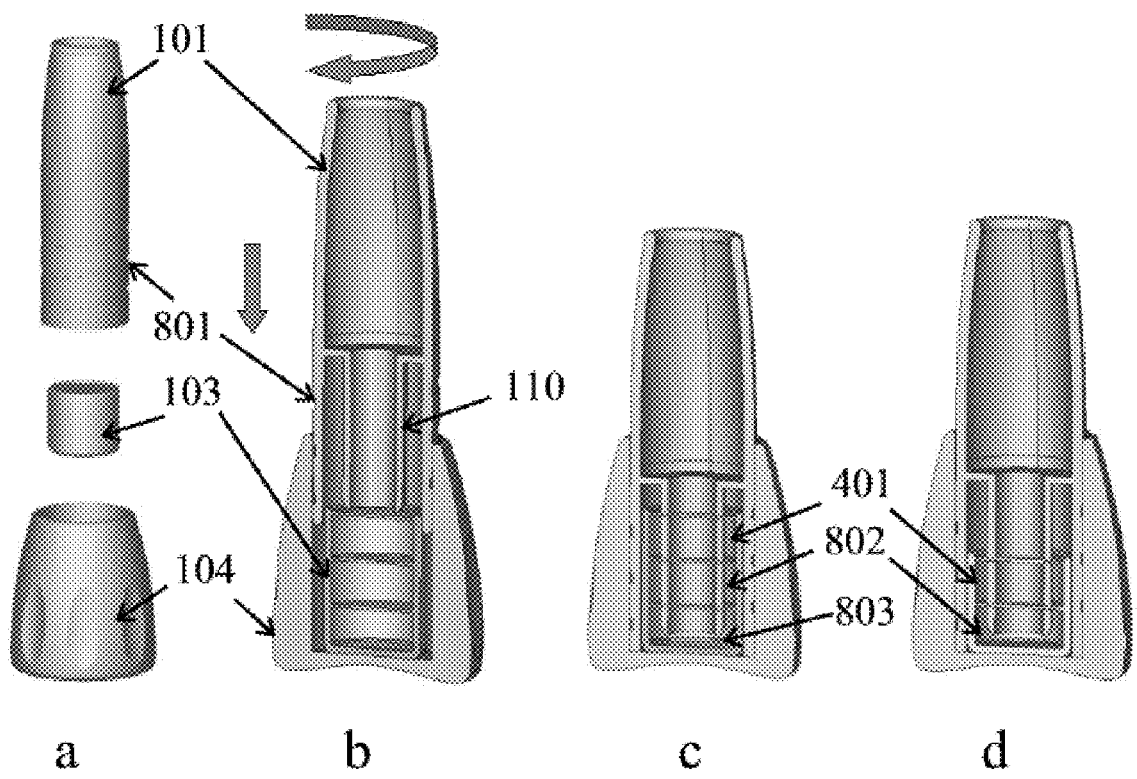
FIG. 8 illustrates a preferred embodiment of a respiratory drug delivery system.
Figure 9:
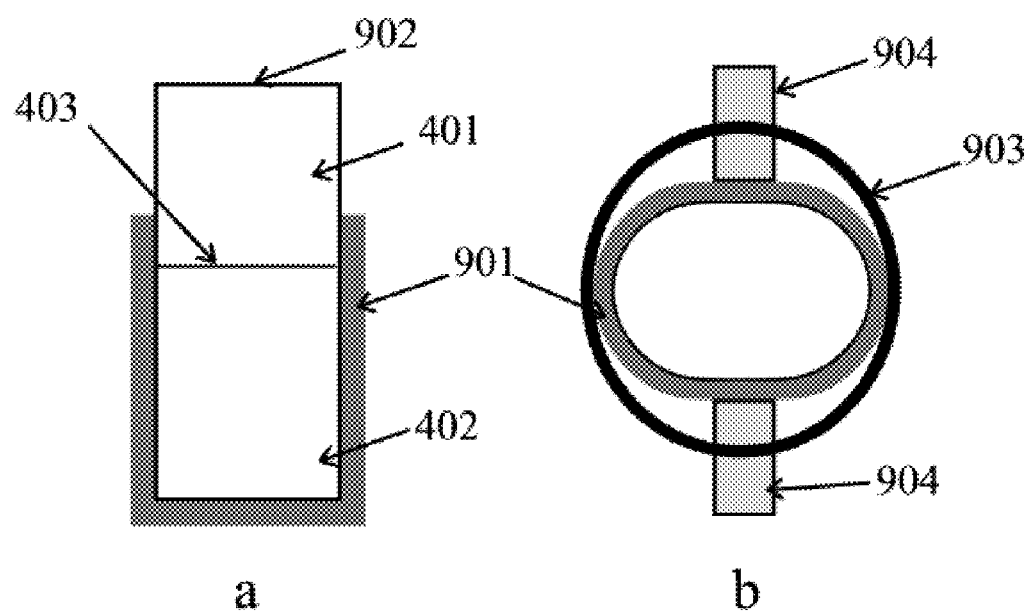
FIG. 9-*a* illustrates a drug and propellant cartridge with a puncture resistant cover according to one aspect of the invention.

Optionally, drug compartment 401 and/or propellant compartment 402 are divided into sub-compartments 406, as shown in FIG. 4b. The staggered multi-tubing piercing mechanism described above operates in conjunction with a partitioned drug compartment 401 and partitioned propellant compartment 402. The drug residing in the drug sub-compartment 406 corresponding to the longer pierce tubing 110 is pierced, aerosolized and delivered first, followed by the drug residing in the drug sub-compartment 406 corresponding to the shorter pierce tubing 110, resulting in overall staggered drug delivery, useful for users who take drugs to be delivered in staggered fashion. Optionally, partitioned drug compartments 401 and/or propellant compartments 402 operate in conjunction with non-staggered multi-tubing pierce mechanism for simultaneous delivery of drugs which are to be stored separately (in separate sub-compartments 406) to avoid mixing prior to aerosolization. Optionally, drug compartments and/or propellant compartments are divided into more than two sub-compartments 406, operating in conjunction with staggered or non-staggered multi-tubing pierce mechanisms.

FIG. 4-*c* is a diagram illustrating a drug cartridge with a drug reservoir, according to one embodiment of the present invention. Drug reservoir 420 allows for placement of one or more drug packages (such as a drug capsule, a drug blister package or other package containing a drug) above propellant compartment 402. Activating piercing trigger 102 will move pierce tubing 110 towards drug package placed in drug reservoir 420, and the piercing of drug package followed by the piercing of propellant compartment 402 aerosolizes the drug for respiratory delivery. Optionally, reservoir 420 allows for placement of drug powder, or other substance to be aerosolized, directly into reservoir 420, for subsequent piercing of propellant compartment 402 and aerosolization of said drug powder or other substance. For example, user can take a capsule containing a drug powder, empty the contents of the capsule into drug reservoir 420, and aerosolize drug powder by activating piercing trigger 102 and piercing propellant compartment 402, resulting in respiratory delivery of drug.

FIG. 4-*d* is a diagram illustrating a drug cartridge with two drug compartments and one gas compartment. Compartments 401, 404, and 402 are separated by membranes 403. In one embodiment, compartments 401 and 404 contain drugs, while compartment 402 contains a propellant as described above. The drug in compartment 401 may be different from the drug in compartment 404, and the two drugs may be unsuitable for mixed storage, but may require mixing when delivered to user. In another embodiment, compartment 401 contains a drug, compartment 404 contains a propellant, and compartment 402 contains a chaser, with the compartments separated by membranes 403. Alternatively, cartridge comprises multiple drug and/or propellant and/or chaser compartments stacked in an order according to any desired sequence of piercing, drug aerosolization and respiratory drug delivery.

Optionally, cartridge 103 has one compartment only, for example containing Oxygen, Nitrous Oxide, other gas or substance, or combination of gases, for respiratory delivery. Alternatively, and for improved delivery and/or deposition of said contents, cartridge 103 has an additional compartment containing a chaser.

FIG. 4-*e* is a diagram illustrating a multi-dose rotary cartridge configuration, according to one embodiment of the present invention. Multiple cartridges 103 are assembled in weekly, monthly or other regular dosing in rotary configuration 407. Optional opening 405 provides opening for mounting body 101 on rotary configuration 407. Shape, size or location of opening 405, or distance between two or more openings 405, serve as key for mounting matching body 101. In one embodiment, opening 405 and body 101 are drug specific, such that only an appropriate body 101 and keyed cartridge 103 pair will fit to deliver a specific drug to a user in possession of the appropriate body/cartridge combination. In another embodiment, body 101 or opening 405 are age-group specific (such as for children or adults), user specific (such as for a specific person), or specific to other user attribute for limiting use to users with said attribute, or for serving as safety feature preventing accidental or intentional misuse of drug cartridge 103.

FIG. 4-*f* is a diagram illustrating a roll-up linear cartridge configuration, according to one embodiment of the present invention. Cartridges 103 are assembled in a multi-cartridge roll-up configuration. Optional keyed detail 405 provides mounting point for appropriate body 101, with optional drug specific keyed detail 405 and body 101 as described above.

FIG. 4-*g* is a diagram illustrating a cartridge configuration with flow resistance flaps 410, according to one embodiment of the present invention. Flexibility and/or surface area of flaps 410 provides inspiratory flow resistance resulting in maximal drug deposition through inspiration by user. Optionally, cartridge 103 comprises flaps 410 with pre-configured flexibility and/or according to user need, for example less flexible flaps 410 for adults and more flexible flaps 410 for children (who have lower lung capacity compared to adults).

FIG. 5-*a* is a diagram illustrating a micro-version 130 of the respiratory drug delivery system, according to one embodiment of the present invention. The micro-version 130 does not have a separate piercing trigger. Instead, the body 131 contains the piercing mechanism with one or more tubings 110 at one end of the body and as shown in FIG. 5-*a*. User pushes cartridge 103 and body 131 against each other while holding mouth to other end of body 131 serving as mouthpiece 113, resulting in piercing of the cartridge 103 compartments by pierce tubing 110 and subsequent respiratory delivery of drug. The micro-version 130 is suitable for use in environments demanding a compact drug delivery system, such as for soldiers in battle or for mountain climbers with minimal space for carrying equipment. FIG. 5-*b* shows the micro version 130 of the respiratory drug delivery system piercing drug cartridge 103.

FIG. 6 is a diagram illustrating optional locators on drug cartridge 103, according to one embodiment of the present invention. Optionally, drug cartridge 103 has one or more cartridge locators 601 to aid in properly aligning body 101 (and/or micro-version body 131) with drug cartridge 103 for piercing, using one or more corresponding body locators 602. Cartridge locators 601 are optionally drug specific. Varying the number and/or shape and/or size of cartridge locators 601 and/or the spacing between cartridge locators 601 results in a "key" which must be matched by corresponding body locators 602 on body 101 (or on micro-version body 131) for proper alignment and piercing of cartridge 103. This key can be drug specific, age-group specific (such as for children or adults), user specific (such as for a specific person), or specific to other user attribute for limiting use to users possessing said attribute, or for serving as safety feature preventing accidental or intentional misuse of drug cartridge 103. For example, a child having her own respiratory drug delivery system with properly keyed body 101 (i.e. keyed for children) is prevented from using an adult drug cartridge 103 if the adult drug cartridge 103 is properly keyed for adults.

FIG. 7 is a flow chart illustrating a method for respiratory drug delivery, according to one embodiment of the present invention. Place 701 cartridge 103 in the respiratory drug delivery system 100. Activate piercing trigger 102 to pierce 702 drug compartment 401 and to pierce 703 propellant compartment 402, resulting in aerosolization and de-agglomeration of drug and respiratory delivery 704 of drug.

Step 701 may be optional or unnecessary if the respiratory drug delivery system is pre-packaged with a cartridge 103 (for example at time of manufacturing or distribution), such as for example a disposable respiratory drug delivery system or a respiratory drug delivery system prepared (i.e. pre-loaded with a cartridge 103) for a user by a nurse, a health care provider, a doctor or other service provider.

FIG. 8 depicts a specific embodiment of a respiratory drug delivery system. As shown in panel a cartridge 103 fits in cartridge holder 104. Body 101 can then be assembled with the cartridge holder 104 for operation. Panel b shows a cross section of the system with body 101 engaged with cartridge holder 104, which is loaded with cartridge 103. Body 101 comprises a body thread 801, and cartridge holder 104 comprises a matching holder thread (not labeled). Threadable engagement of body 101 to cartridge holder 104, as represented by the curved arrow atop panel b results in movement of the body structure towards cartridge 103, as depicted by the wide arrow to the left of panel b. Body 101 comprises pierce tubing 110. Pierce tubing 110 may be cylindrical, with an external diameter slightly lower than the internal diameter of a cylindrical cartridge. In operation, assembly of body 101 to loaded cartridge holder 104 results in tubing 110 being positioned, as shown in panel b, to penetrate cartridge 103. The drug compartment 401 is pierced first, followed by the propellant compartment 802 as shown in panel d, through the common membrane (not labeled). In some embodiments, as shown in panel c, this is followed by piercing of the chaser compartment 803 through the chaser-propellant membrane (not labeled). Piercing in some embodiments is accomplished by continued threading of body 101 to cartridge holder 104. Markings may be provided on the body 101 and possibly cartridge holder 104 to indicate when piercing occurs. Alternatively, the system may be positioned for operation as depicted in panel b, and a pierce trigger (102) mechanism is in place for completing the later operation steps.

FIG. 9-*a* depicts another embodiment of a cartridge. Drug compartment 401 is joined to propellant compartment 402 by a common membrane 403. A puncture resistant, flexible cover 901 envelops part of the propellant compartment. The purpose of the cover is to allow a constriction mechanism to apply pressure to the propellant compartment without rupturing the envelope of the propellant compartment. As such, the puncture resistant portion of the cover 901 may cover only one small area where a pin could be pushed against the propellant compartment, may cover two or more distinct patches, may cover a ring around a cylindrical propellant compartment, may cover the entire external area of the propellant compartment as shown in FIG. 9-*a*, and may additionally cover part of the drug compartment. The puncture resistant, flexible cover 901 need not be a distinct layer of the propellant compartment; it may be itself the wall of the propellant compartment. Suitable materials and dimensions for puncture resistant covers will depend on specific applications, as will the pressure to which the common membrane is sensitive and the specific constriction mechanism for which the cartridge is intended.

A common membrane 403 joins the drug and propellant compartments. Membrane is pressure sensitive, i.e. it is designed to withstand the pressure in the propellant compartment, but will break at a higher, predetermined pressure. Any known method, or combination of methods, of accomplishing this may be used in making the common membrane. For example, one way of accomplishing this is using a puncture resistant cover enveloping only the entire outer walls of the propellant compartment, but to not the common membrane. Another way is to have the common membrane of an identical material as the outer walls but thinner, so that high propellant compartment pressure will predictably break the common membrane first. Another way of making the membrane pressure sensitive is to carve or otherwise form grooves into the common membrane but not the outer membranes or walls, which will define the rupture sites when propellant compartment pressure is increased. In operation, when the predetermined pressure to which the common membrane is designed to be sensitive is reached or exceeded in the propellant compartment, the common membrane breaks and propellant flows through the drug compartment as described below.

Another feature of the cartridge shown in FIG. 9-*a* is drug ejection membrane 902. In some embodiments this membrane is intended to be pierced prior to breaking the common membrane. In other embodiments the membrane contains pores or openings of any shape or size. In these embodiments the drug ejection membrane is covered by a protective foil, which is removed before use of the cartridge. In some embodiments the drug ejection membrane has pores of defined sizes, such as about 10 μm, 7.5 μm, but may be less that 5 μm, such as in the range of 0.1 μm to 5 μm. These pores define cut off sizes for the aerosolized particles that leave the drug compartment, and pore sizes may be adjusted for drug formulations according to their desirable mass median diameters. In some embodiments the drug ejection membranes are pressure sensitive, and are sensitive to a lower pressure than the common membrane. Generally for these embodiments, the drug compartment contains excessive enveloping membrane, such as by packing the drug under low pressure. This is so that during operation, constriction of the adjacent propellant compartment will not significantly increase the pressure within the drug compartment, thus allowing the common membrane to break. The drug ejection membrane may be made pressure sensitive as described above for the common membrane. The drug ejection membrane is typically sensitive to a pressure significantly lower than the pressure to which the common membrane is sensitive. As a result, breaking of the drug ejection membrane occurs virtually simultaneously with breaking of the common membrane, so that pressure in the drug compartment is much lower than that in the propellant compartment when the drug ejection membrane breaks. As a result, propellant will flow from the propellant compartment through the drug compartment, and out through the broken drug ejection membrane, and is then made available for inhalation.

FIG. 9-*b* is a top view of a cartridge chamber with a constricting mechanism, which is part of a respiratory drug delivery system using cartridges encased in puncture resistant flexible covers. Cartridge chamber 903 is typically enclosed within a body 101 and/or base 104, and comprises a lumen of a shape generally matching that of the intended cartridge. A mechanism operable form outside the system constricts the lumen of chamber 903. Shown in FIG. 9-*b* are two pins 904 that push against opposite sides of cartridge cover 901. However, many other embodiments can be envisioned, such as with a single pushing pin, as well as with more than two pins. The pins at the zone of contact with the propellant compartment can have a smooth or otherwise enlarged surface to avoid placing puncturing stress on the cover. One or more handles or other strength-enhancing device may facilitate operation of a constricting mechanism, such as insertion of pins 904 within the lumen of chamber 903, so that any user can supply the force necessary for operation. The constricting mechanism squeezes and thereby applies additional pressure to the propellant chamber of the cartridge. As a result, the pressure in the propellant compartment will equal or exceed the pressure to which the common membrane is sensitive, and the common membrane will break. Systems for respiratory drug delivery that have a chamber constricting mechanism may also have a piercing mechanism for piercing the drug ejection membrane, as for some of the cartridges described above.

Figure 10:
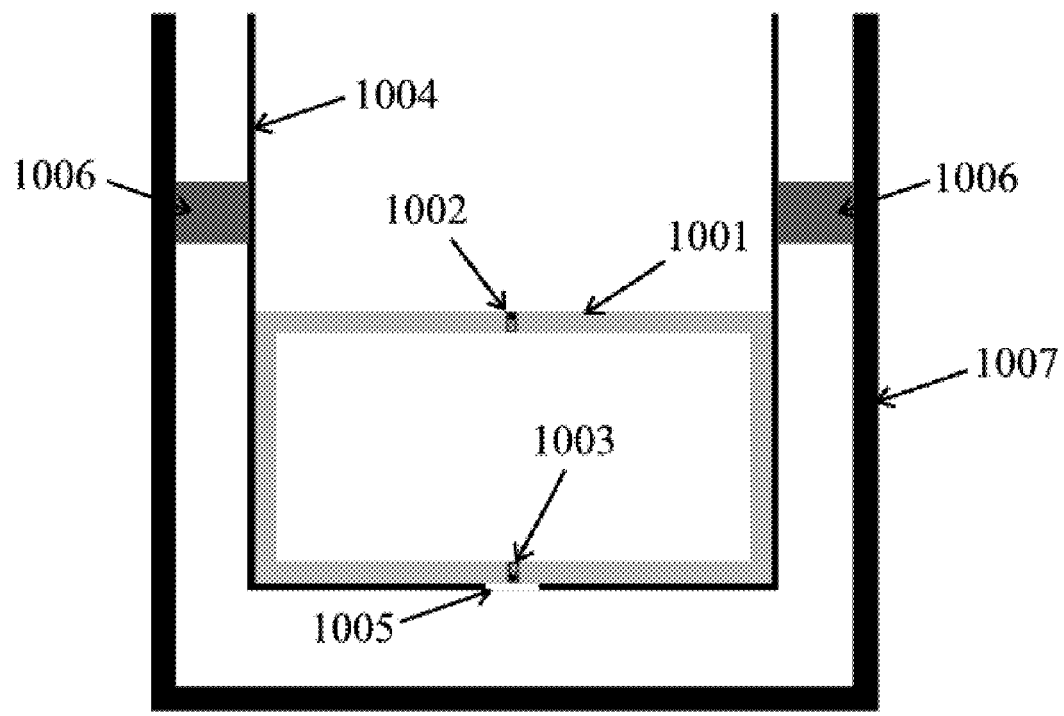
FIG. 10 shows a system with a reusable propellant tank.
Figure 11:
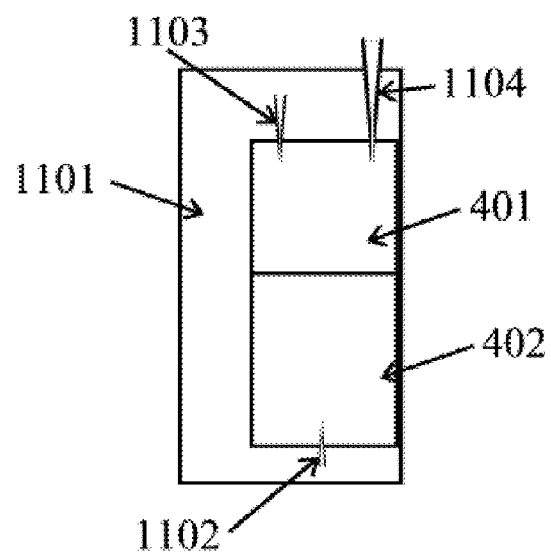
FIG. 11 illustrates an embodiment of a system with a propellant chamber.

FIG. 10 depicts a reusable propellant tank, which is part of some embodiments of a respiratory drug delivery system. Reusable tank 1001 typically has rigid walls for enclosing a fixed volume of propellant. A propellant filling valve 1003 provides a route for injecting propellant into the tank, and a propellant release valve 1002 is operated to release the propellant. The two valves may have distinct openings as shown in FIG. 10, although in some embodiments the same tank opening is adapted to function as both filling and release valve. The tank typically is intended to contain a dose of propellant suitable for aerosolizing a single dose of a drug. The amount of propellant loaded in the tank, and the resulting pressure, can vary depending on the drug, patient, or any other factor. The system also has a drug chamber, similar to drug reservoir 420 described above. The drug chamber is in fluid communication with the release valve. As a result, during operation when the release valve is open, propellant flows through the drug chamber, aerosolizing the drug. The drug chamber also has a drug ejection opening, through which the aerosol flows and is made available for respiratory delivery.

One embodiment further illustrated in FIG. 10 comprises a tank filling mechanism. Refillable tank 1001 is hermetically sealed within walls 1004, with an opening 1005 exposing only the filling valve 1003. A movable seal 1006, such as an O-ring, is placed between walls 1004 and an outer casing 1007. The seal 1006 can be moved so as to increase the pressure outside filling valve 1003. When this operation is performed, valve 1003 opens filling the tank with propellant. Movement of the seal 1006 can be coupled to movement of a body 101 and a holder 104 during assembly of the system.

In some embodiments a kit is provided with a system comprising a reusable propellant tank as described above, and a syringe for filling the tank. The syringe may inject a desired volume of air into the propellant tank, or may be pre-filled with a necessary volume of a propellant of a suitable composition for the drug to be administered.

FIG. 11 illustrates an embodiment of a system with a propellant chamber. A propellant compartment 402 contains an amount of propellant suitable for aerosolizing a single dose of a drug. The system comprises a propellant chamber 1101. When a cartridge is inserted, the propellant chamber hermetically seals the propellant compartment of the cartridge within the propellant chamber. A propellant releasing mechanism 1102 such as a pin or tubing is operable to release the propellant within the propellant chamber. At this point the propellant pressure is at a desirable level for aerosolizing the drug, usually above atmospheric pressure. A drug compartment 401 is at least partly in contact with the propellant chamber, though it may be entirely enclosed in the propellant chamber as shown in FIG. 11. The drug compartment may be joined to its matching propellant compartment, as illustrated in FIG. 11, although in some embodiments they are provided and used separately. A piercing mechanism allows flow of propellant from the propellant chamber into the drug compartment and out of the drug compartment, where it is made available for respiratory delivery. As illustrated in FIG. 11, pierce tubing 1103 penetrates a drug compartment membrane, thus making a fluid connection between the propellant chamber and the drug compartment. Pierce tubing 1104 also penetrates the drug compartment, forming a fluid connection between the drug compartment and a system component, such as a spacer, outside the propellant chamber (not shown in FIG. 11). Tubing 1104 forms a hermetical seal with the propellant chamber so that propellant exits the propellant chamber only through the lumen of tubing 1104. The drug membrane need not necessarily be pierced at different locations, as bound parallel tubing may be employed with a single piercing tip, or concentric tubing, or a structure as described for example in U.S. Pat. No. 6,901,929. Different embodiments have mechanisms designed to pierce the propellant and drug compartment membranes in different series.

The invention provides several advantages compared to current related technologies, although all advantages are not necessarily present in every embodiment of the invention. In many embodiments relate to respiratory drug delivery systems that are quite compact and light. Due to their reduced size, they can be conveniently carried and used, facilitating compliance with drug administering regimens. For the most part the disclosed devices can be made out of inexpensive materials using established processes, thus having a low cost of production. Moreover, the devices are made up of a low number of components. Consequently, the cost of the drug delivery systems should be low, making them either disposable or readily replaceable after a limited useful lifetime. This is especially important because aerosolized drugs often deposit on passageways of devices extensively used, affecting characteristics of aerosol formation and delivery flow. Moreover, disposable systems are particularly desirable for treatments based on single or limited dose drug administration. Limited use of inexpensive devices also eliminates concerns with wear and tear of similar systems. The absence of a pump for pressurizing air in most embodiments allows not only for low production cost, but also ease of operation by many groups of patients, such as children, elderly, or those with clubbed fingers. Use of the disclosed systems ensures consistent preparation of the aerosolized medicament for every operation, and consequently reliable respiratory administration of the drug. For many embodiments use of propellants and chasers, as well as other device features, limit the necessity for vigorous inspiration, which could be difficult for patients with certain physical or pathological conditions. Absence of a canister of pressurized propellant and/or chaser ensures time dependent consistency of dose preparation and delivery. The inexpensive design and simple operation of the disclosed systems also makes adaptation of the design of systems for use by children readily feasible.

All cited documents, including patents, patent applications, and other publications are incorporated herein by reference in their entirety.

Foregoing described embodiments of the invention are provided as illustrations and descriptions. They are not intended to limit the invention to precise form described. Other variations and embodiments are possible in light of above teachings, and it is thus intended that the scope of invention not be limited by this Detailed Description, but rather by Claims following.

What is claimed is:

1. A cartridge comprising:

a puncture resistant flexible cover;

a drug compartment containing a single dose of a drug; and a propellant compartment containing a propellant in a quantity suitable for aerosolizing the single dose of the drug, the propellant compartment being partly enveloped within the cover to prevent puncture of the propellant compartment during aerosolizing;

wherein the drug compartment and propellant compartment are joined by a common membrane, and the drug compartment is capable of being broken or pierced to eject the single dose of the drug from the cartridge during aerosolizing such that the drug is made available for delivery.

2. The cartridge of claim 1, wherein the drug compartment comprises two or more drug sub-compartments.

3. The cartridge of claim 1, further comprising one or more locators for proper alignment of the cartridge with a respiratory drug delivery system body, wherein the shape or size or spacing or number of the one or more locators serves as a safety key for matching by a similarly keyed respiratory drug delivery system body.

4. The cartridge according to claim 1 further comprising a chaser compartment containing a chaser, wherein the chaser compartment is joined to the propellant compartment by a chaser-propellant membrane.

5. A system for respiratory delivery of a drug contained in a cartridge, the system comprising:
a cartridge comprising a drug compartment containing a single dose of a drug, and a propellant compartment containing a propellant in a quantity suitable for aerosolizing the single dose of the drug, wherein the drug compartment and propellant compartment are joined by a common membrane;
a cartridge holder for holding the cartridge, the holder having a holder thread; and
a body with a pierce tubing, the body having a body thread, wherein engagement of the holder thread to the body thread positions the pierce tubing for consecutive piercing of first the drug compartment and second the propellant compartment through the common membrane.

6. The system according to claim 5 wherein insertion of pierce tubing through the drug compartment and the common membrane is accomplished by engagement of the holder thread to the body thread.

7. A system for respiratory delivery of a drug contained in a cartridge, the system comprising:
a cartridge comprising a drug compartment containing a single dose of a drug, a propellant compartment containing a propellant in a quantity suitable for aerosolizing the single dose of the drug, and a chaser compartment containing a chaser, wherein the drug compartment and propellant compartment are joined by a common membrane, and wherein the chaser compartment is joined to the propellant compartment by a chaser-propellant membrane;
a cartridge holder for holding the cartridge, the holder having a holder thread; and a body with a pierce tubing, the body having a body thread, wherein engagement of the holder thread to the body thread positions the pierce tubing for consecutive piercing of first the drug compartment, second the propellant compartment through the common membrane, and third the chaser compartment through the chaser-propellant membrane.

8. The system according to claim 7 wherein insertion of pierce tubing through the drug compartment, the common membrane, and the chaser-propellant membrane is accomplished by engagement of the holder thread to the body thread.

9. A system for respiratory delivery of a drug contained in a cartridge according to claim 1, the system comprising:

a propellant chamber comprising a propellant releasing mechanism,
a propellant tube for connecting the propellant chamber to the drug compartment, and
a drug ejection tube for transporting aerosolized drug from the drug compartment to a body, wherein operation of the propellant releasing mechanism releases the propellant into the propellant chamber and causes the propellant to flow through the propellant tube into the drug compartment and through the drug ejection tube into the body.

10. A cartridge according to claim 1, wherein further:
the drug compartment comprises a drug ejection membrane;
the propellant is pressurized; and
the common membrane is pressure sensitive, whereby a predetermined pressure applied to the cover breaks the common membrane.

11. The cartridge according to claim 10 wherein the drug ejection membrane is sensitive to a lower pressure than the common membrane, whereby breaking of the common membrane results in breaking of the drug ejection membrane before drug compartment pressure equals propellant compartment pressure.

12. A system for respiratory delivery of a drug contained in a cartridge according to claim 10, the system comprising:
a body with a cartridge chamber; and
a cartridge chamber constricting mechanism capable of constricting the cover so that the pressure in the propellant compartment reaches or exceeds the predetermined pressure.

13. The system according to claim 12 further comprising a piercing mechanism for piercing the drug ejection membrane.

14. A method for respiratory drug delivery comprising:
providing a cartridge according to claim 10,
piercing the drug ejection membrane, and
constricting the cover to break the common membrane, thereby ejecting aerosolized drug through the drug ejection membrane for respiratory delivery.

15. A method for respiratory drug delivery comprising:
providing a cartridge according to claim 11, and
constricting the cover to break the common membrane and the drug ejection membrane, thereby ejecting aerosolized drug through the drug ejection membrane for respiratory delivery.

16. A respiratory drug delivery system, comprising:
a propellant tank of a fixed volume for containing a propellant in a quantity suitable for aerosolizing the single dose of a drug, the propellant tank having a filling valve and a release valve; and
a drug chamber for holding the single dose of the drug, the drug chamber being in fluid communication to the release valve of the propellant tank, the drug compartment also having a drug ejection opening, such that opening the release valve of a pressurized tank causes the propellant to flow through the drug chamber and ejects aerosolized drug through the drug ejection opening.

17. A kit comprising:
the respiratory drug delivery system according to claim 16, and
a syringe for filling the drug with propellant via the filling valve.

* * * * *